United States Patent [19]
Vasudevan et al.

[11] Patent Number: 6,093,838
[45] Date of Patent: Jul. 25, 2000

[54] AMINES SUBSTITUTED WITH A DIHYDRO-BENZOFURANYL OR WITH A DIHYDRO-ISOBENZOFURANYL GROUP, AN ARYL OR HETEROARYL GROUP AND AN ALKYL GROUP, HAVING RETINOID-LIKE BIOLOGICAL ACTIVITY

[75] Inventors: Jayasree Vasudevan, Irvine; Richard L. Beard, Newport Beach; Dehua Huang, San Diego; Roshantha A. Chandraratna, Mission Viejo, all of Calif.

[73] Assignee: Allergan Sales, Inc., Irvine, Calif.

[21] Appl. No.: 09/375,845

[22] Filed: Aug. 16, 1999

[51] Int. Cl.[7] ................ C07D 307/78; C07D 409/00
[52] U.S. Cl. ............... 549/467; 549/60; 546/284.1; 544/322; 548/190; 548/311.4
[58] Field of Search ............ 549/467, 60; 546/284.1; 548/190, 311.4; 544/322

[56] References Cited

U.S. PATENT DOCUMENTS

| | | | |
|---|---|---|---|
| 5,455,265 | 10/1995 | Chandraratna | 514/448 |
| 5,616,712 | 4/1997 | Teng et al. | 546/158 |
| 5,877,207 | 3/1999 | Klein et al. | 514/456 |

FOREIGN PATENT DOCUMENTS

| | | |
|---|---|---|
| 93/11755 | 6/1993 | WIPO . |
| 98/45242 | 10/1998 | WIPO . |

OTHER PUBLICATIONS

Dawson and William H. Okamura, *Chemistry and Biology of Synthetic Retinoids*, published by CRC Press, Inc., 1990, pp. 334–335.
Verma & Boutwell, Cancer Research, (1977), 37, 2196–2201.
Cancer Research: 1662–1670 (1975).
Feigner P. L. and Holm M. (1989) Focus, 112.
Heyman et al., Cell 68, 397–406 (1992).
Allegretto et al., J. Biol. Chem. 268, 26625–26633.
Mangelsdorf et al., The Retinoids: Biology, Chemistry and Medicine, pp. 319–349, Raven Press Ltd., New York.
Cheng et al., Biochemical Pharmacology vol. 22 pp. 3099–3108.
Klein et al., J. Biol. Chem. 271, 22692–22696 (1996).
Chen et al. (1987) Mol. Cell. Biol. 7, 2745–2752.
de Wet (1987) Mol. Cell. Biol. 7, 725–737.
Nagpal et al., Embo J. 12, 2349–2360 (1993).
Corey, E. J. Schmidt, G., *Tet. Lett.*, 399 (1979).
Omura, K., Swern, D., *Tetrahedron*, 1978, 34, 1651.
Bennett et al. in J. Chem. Soc., 1936, 1114.
J. Med. Chem., 1998, 41, 1124–1137.

*Primary Examiner*—Amelia Owens
*Attorney, Agent, or Firm*—Gabor L. Szekeres; Robert J. Baran; Martin A. Voet

[57] ABSTRACT

Compounds of Formula 1 and of Formula 2

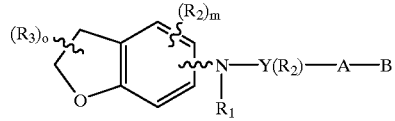

Formula 1

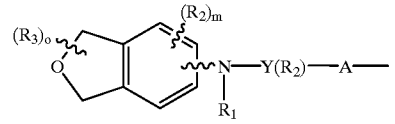

Formula 2 where the symbols have the meaning defined in the specification, have retinoid-like biological activity.

26 Claims, No Drawings

AMINES SUBSTITUTED WITH A DIHYDRO-BENZOFURANYL OR WITH A DIHYDRO-ISOBENZOFURANYL GROUP, AN ARYL OR HETEROARYL GROUP AND AN ALKYL GROUP, HAVING RETINOID-LIKE BIOLOGICAL ACTIVITY

BACKGROUND OF THE INVENTION

1. Field of the Invention

The present invention relates to novel compounds having retinoid-like biological activity. More specifically, the present invention relates to amines substituted with a dihydro-benzofuranyl or with a dihydro-isobenzofuranyl group, an aryl or heteroaryl group and an alkyl group, which have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

Although pharmaceutical compositions containing retinoids have well established utility, retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXF_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having Negative Hormone and/or Antagonist Activities" describes the foregoing two-state model and the use of retinoid antagonist and negative hormones in detail.

Among the scientific publications Dawson and William H. Okamura, *Chemistry and Biology of Synthetic Retinoids*, published by CRC Press Inc., 1990, pages 334–335, 354 and 324–356 is of special interest as an overview of the prior art on the subject.

Among United States and foreign patents which disclose compounds having retinoid agonist, antagonist or inverse agonist like biological activity and are known to applicant the following examples include diaryl or heteroaryl substituted amines and are therefore of interest as background to the present invention: WO9845242-A1, published on Oct. 15, 1998, and French patent application number 94 05019, laid-over-to-public-inspection on Oct. 27, 1995.

SUMMARY OF THE INVENTION

The present invention relates to compounds of Formula 1 and of Formula 2

Formula 1

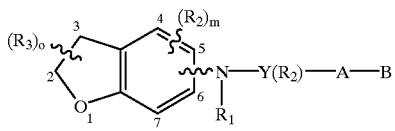

Formula 2

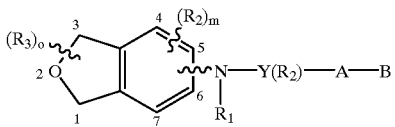

where $R_1$ is H, alkyl of 1 to 10 carbons, phenyl, heteroaryl, phenyl-$C_1$–$C_6$ alkyl, $C_1$–$C_6$-alkylphenyl, heteroaryl-$C_1$–$C_6$ alkyl, $C_1$–$C_6$-alkylheteroaryl where heteroaryl is selected from the group consisting of pyridyl, thienyl, furyl, pyridazinyl, pyrimidinyl, pyrazinyl, thiazolyl, oxazolyl, imidazolyl and pyrrazolyl;

$R_2$ is independently H, alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer having the values of 0 to 3;

$R_3$ is independently H, alkyl of 1 to 6 carbons, or F;

o is in an integer having the values of 0 to 4;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, tri-lower alkylsilyl, OH, $OR_8$ or $OCOR_8$ where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

In a second aspect, this invention relates to the use of the compounds of Formula 1 or of Formula 2 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases such as type II non-insulin dependent diabetes mellitus (NIDDM) and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be co-administered with retinoids. The retinoid antagonist and inverse agonist compounds of the present invention are also useful in the treatment of acute or chronic toxicity resulting from over-dose or poisoning by retinoid drugs or Vitamin A.

Generally speaking, the second aspect of the invention relates to the use of the novel compounds to prevent or treat diseases and conditions which are responsive to compounds that promote the expression of or bind to receptors belonging to the steroid or thyroid receptor superfamily.

This invention also relates to a pharmaceutical formulation comprising a compound of Formula 1 or a compound of Formula 2 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and a decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in *Cancer Research*: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$ receptors, and the ability or inability of the compounds to activate transcription of a reporter gene through these receptor subtypes can be tested. These assays are expected to demonstrate that the compounds of the present invention act as agonists of one or more of the above-described receptors. However, some of the compounds of the invention may behave as retinoid antagonists or partial antagonists and/or as inverse agonists. Because of the complex distribution of the different retinoid receptors in various organs of the mammalian body partial agonists and partial antagonists and compounds which have the characteristics of both may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. *Cell* 68, 397–406, (1992); Allegretto et al. *J. Biol. Chem.* 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-P-GR holoreceptor Transactivation Assay

CV-1 cells ($4 \times 10^5$ cells/well) were transiently transfected with the luciferase reporter plasmid MTV-4(R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 µl instead of 100 µl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed and luciferase activity was measured as previously described in de Wet (1987) Mol. Cell. Biol. 7, 725–737. Luciferase values represent the mean±SEM of triplicate determinations normalized to β-galactosidase activity.

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. *J. Biol. Chem.* 271, 22692–22696 (1996) which is expressly incorporated herein by reference. In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-16, an ER-RXRα chimeric receptor and an ERE-tk-Luc chimeric reporter gene to produce a basal level of luciferase activity, as shown by Nagpal et al. *EMBO J.* 12, 2349–2360 (1993) expressly incorporated herein by reference. Retinoid inverse agonists are able to inhibit the basal luciferase activity in these cells in a dose dependent manner and $IC_{50}$s measured. A detailed description of the tests used for determining whether or not a compound is a retinoid antagonist or inverse agonist, and the manner of utilizing retinoid antagonists and inverse agonists is provided in U.S. Pat. No. 5,877,207, the specification of which is expressly incorporated herein by reference.

Table 1 discloses the activity of certain exemplary compounds of the invention in the above-described chimeric receptor transactivation assay, holoreceptor transactivation assay and a ligand binding assays. Particularly, the transactivation data pertaining to RAR receptors were obtained in the chimeric assay, and the data pertaining to transactivation of RXR receptors were obtained in the holoreceptor transactivation assay.

| COM-POUND NUMBER | RAR Trans. $EC_{50}$ (nM) RAR Bind. $K_i$ (nM) | | | RXR Trans. $EC_{50}$ (nM) RXR Bind $K_i$ (nM) | | |
|---|---|---|---|---|---|---|
| | α | β | γ | α | β | γ |
| 26 | NA | NA | NA | NA | NA | NA |
| | >30k | >30k | 6.7k | 10k | >100k | >100k |
| 27 | NA | NA | NA | 1k (80) | >1k | >1k |
| | 30k | >30k | >30k | 15k | >100k | >100k |
| 41 | NA | NA | NA | 1k (75) | NA | NA |
| | >30k | >30k | >30k | 9.2k | >100k | >100k |
| 30 | NA | NA | NA | 1k (75) | >1k (10) | >1k (70) |
| | 16k | >30k | 3.3k | 11k | 4.6k | >10k |
| 31 | NA | NA | NA | 74 (116) | 1k (75) | 85 (125) |
| | 25k | 29k | 4k | 1.8 | 752 | 4.1k |
| 32 | NA | NA | NA | 98 (103) | 1k (50) | 230 (122) |
| | >1k | >1k | 2k | 222 | 342 | 672 |
| 44 | NA | NA | NA | 22 (73) | 171 (33) | 20 (48) |
| | >1k | >1k | 1.6k | 11 | 215 | 344 |

-continued

| COM-POUND NUMBER | RAR Trans. $EC_{50}$ (nM) RAR Bind. $K_i$ (nM) | | | RXR Trans. $EC_{50}$ (nM) RXR Bind $K_i$ (nM) | | |
|---|---|---|---|---|---|---|
| | α | β | γ | α | β | γ |
| 43 | NA | NA | NA | 16 (66) | 58 (58) | 19 (108) |
| | >10k | >10k | 2.6k | >1k | >1k | >1k |
| 28 | NA | NA | NA | >1k (25) | NA | >1k (15) |
| | 9.4k | >10k | 4.5k | >10k | >10k | >10k |
| 29 | NA | NA | NA | 139 (117) | 800 (70) | 692 (130) |
| | >10k | >10k | 8.4k | >1k | >1k | >1k |
| 42 | NA | NA | NA | 203 (100) | >1K (30) | 511 (132) |
| | >10k | >10k | 4.9k | >1k | >1k | >1k |
| 73 | NA | NA | | 10 (92) | 71 (92) | 17 (97) |
| | 12k | >10k | 2.7k | 71 | 178 | 236 |
| 70 | | | | 11 (119) | 73 (113) | 18 (120) |
| 83 | NA | NA | NA | 39 (107) | 1k (100) | 63 (140) |
| | >10k | >10k | >10k | 1k | >1k | >1k |
| 84 | NA | NA | NA | 40 (121) | 1k (184) | 51 (124) |
| | >10 | >10k | >10k | 1.5k | 2k | >1k |
| 85 | NA | NA | NA | 161 (122) | 1k (60) | 700 (197) |
| | >10k | >10k | >10k | >1k | >1k | >1k |
| 87 | NA | NA | NA | 57 (115) | 1k (65) | 765 (134) |
| | >10k | >10k | >10k | 650 | 2.7k | 2.1k |

Numbers in parentheses indicate % efficacy relative to $10^{-6}$M ATRA (RARs) or $10^{-6}$M (+)-(1S,2S,1E,2E)-3-Methyl-5-[2-methyl-2-(5,5,8,8-tetramethyl-5,6,7,8-tetrahydro-naphthalen-2-yl)-cyclopropylpenta-2,4-dienoic acid (RXRs)
NA = Not Active As it can be seen from the foregoing assay results the preferred compounds of the invention are specific or selective agonists of RXR receptors.

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness;

providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be administered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC: METHODOLOGY

Definitions

The term alkyl refers to and covers any and all groups which are known as normal alkyl, branched-chain alkyl, cycloalkyl and also cycloalkyl-alkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo- lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 or of Formula 2 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

The term amides has the meaning classically accorded that term in organic chemistry. In this instance it includes the unsubstituted amides and all aliphatic and aromatic mono- and di- substituted amides. Unless stated otherwise in this application, preferred amides are the mono- and di-substituted amides derived from the saturated aliphatic radicals often or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula -CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some compounds of the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

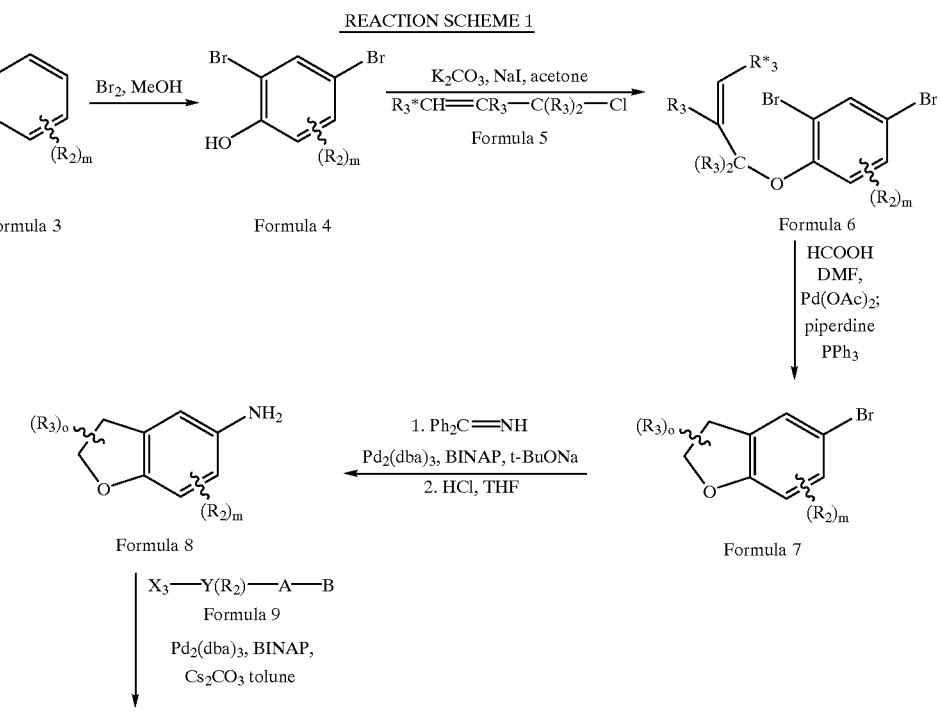

-continued

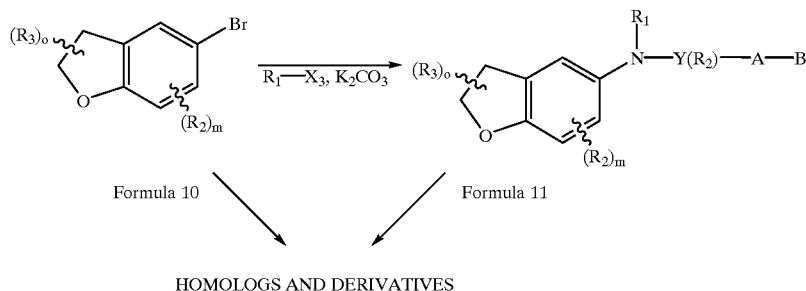

Formula 10   Formula 11

HOMOLOGS AND DERIVATIVES

The compounds of the invention which are dihydrobenzofuran derivatives in accordance with Formula 1 can, generally speaking be obtained by a series of reactions as disclosed in Reaction Schemes 1 and 2. Referring first to Reaction Scheme 1, the starting compound in this synthetic route is a phenol of Formula 3 where the symbols $R_2$ and m are defined as in connection with Formula 1. These phenol compounds can, generally speaking, be obtained in accordance with the chemical scientific and patent literature, or by such modifications of the published literature procedures which will become readily apparent to the practicing synthetic organic chemist. Examples for the starting material of Formula 3 are 2-methyl-phenol, 2-ethyl-phenol and 2-i-propyl-phenol. The compound of Formula 3 is brominated in a suitable solvent, such as methanol, to obtain the 2,4-dibromo-6-alkyl-phenol derivative of Formula 4. Reaction Scheme 1 illustrates the bromo derivative that eventualy gives rise to benzofuran derivatives of the invention where the tertiary amino function is attached to the 5-position of the benzofuran ring. A sequence of reactions analogous to the ones specifically shown in Reaction Scheme 1 can be conducted on an isomeric bromophenol derivative giving rise to benzofurans of the invention where the teriary amino group is attached to the 6 position of the benzofuran moiety.

Returning now to the description of Reaction Scheme 1, the compound of Formula 4 is then reacted with an allyl-chloride (or bromide) derivative of the formula $R*_3CH=CR_3—C(R_3)_2—Cl$ (Formula 5) where the symbol $R_3$ is defined as in connection with Formula 1, and the symbol $R*_3$ is defined as hydrogen or as the group $R_3$ in Formula 1 with one less $CH_2$ unit, that is a homolog having one $CH_2$ unit (carbon atom) less than the group $R_3$. An example for the allyl chloride derivative of Formula 5 that is utilized for the synthesis of several preferred compounds of the invention is 3-chloro-2-methylpropene. The reaction with the allylchloride derivative of Formula 5 is preferably conducted in the presence of sodium iodide and an acid acceptor such as potassium carbonate. The resulting allyloxybenzene derivative of Formula 6 is then ring closed by heating in the presence of acid (HCOOH), palladium(II) acetate, triphenylphosphine and piperidine in an aprotic solvent, such as dimethylformamide, to provide a dihydro-5-bromobenzofurane derivative of Formula 7. The dihydro-5-bromobenzofurane derivative of Formula 7 is reacted first with benzophenone imine in the presence of tris (dibenzylideneacetone)dipalladium(0) $(Pd_2(dba)_3)$, and (S)-(−)-2,2'-bis(diphenylphosphino) 1,1'-binaphthyl (BINAP) acting as catalysts, by heating in toluene under the protective blanket of an inert gas, in the presence of an acid acceptor such as sodium-tert-butoxide and then with hydrochloric acid to yield the dihydro-5-aminobenzofurane derivative of Formula 8. The amino compounds of Formula 8 are then reacted with the reagent $X_3—Y(R_2)—A—B$ (Formula 9) where $X_3$ represents a halogen, preferably iodine or bromine, and the remaining symbols are defined as in connection with Formula 1. The reagents of Formula 9 are halogen substituted aryl or heteroaryl compounds which, generally speaking, can be obtained by reactions well known in the art. An example of such a compound is ethyl-4-iodobenzoate which is obtainable, for example, by esterification of 4-iodobenzoic acid. This esterification reaction is described in U.S. Pat. No. 5,616,712 incorporated herein by reference. Other examples for the reagents of Formula 9 are ethyl 6-iodonicotinate (obtainable by halogen exchange reaction on 6-chloronicotinic acid followed by esterification), ethyl 5-iodo or 5-bromothiophene-2-carboxylate and ethyl 5-iodo or 5-bromoifuran-2-carboxylate. The reaction of the amine compounds of Formula 8 with the halogenated reagent of Formula 9 is conducted in the presence of the catalysts tris (dibenzylideneacetone)dipalladium(0) $(Pd_2(dba)_3)$, and (S)-(−)-2,2'-bis(diphenylphosphino) 1,1'-binaphthyl (BINAP) in the presence of an acid acceptor, such as cesium carbonate, while being heated in an inert solvent (toluene) in an inert gas atmosphere. The resulting aryl or heteroaryl and dihydrobenzofuran-5-yl amines (disubstituted amines) of Formula 10 are within the scope of the invention, but are preferably converted to trisubstituted amines of Formula 11, also within the scope of the invention, by reaction with a reagent of the formula $R_1—X_3$ where $R_1$ is defined as in connection with Formula 1, and $X_3$ is halogen, preferably iodine or bromine. The reaction of the disubstituted amines of Formula 10 with the reagent $R_1—X_3$ will be recognized by those skilled in the art as an "alkylation" or analogous reaction, and is preferably conducted by heating in a solvent, such as dimethylacetamide, in the presence of an acid acceptor, such as potassium carbonate. The resulting trisubstituted amine compounds of Formula 11 include the dihydro-benzofuran-5-yl moiety and are within the scope of the invention. These compounds can be converted into further homologs and derivatives (as indicated in the reaction scheme) still within the scope of the invention, by such reactions as esterification, saponification, homologation, reduction to aldehyde or alcohol stage and the like, which per se are well known in the art. These reactions usually involve transformations of the groups designated A and B in the formulas (see Formulas 1, 2 and 11 for example) but are not necessarily limited to those. Some of the known and published general principles and synthetic methodology employed in the transformations of the A and B groups are briefly described below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature lor about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978. 34. 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

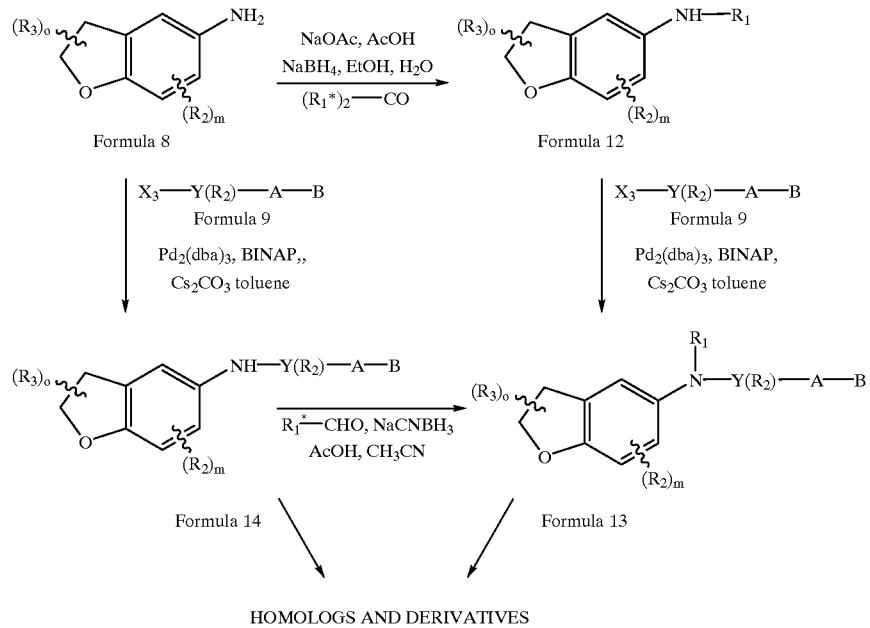

REACTION SCHEME 2

HOMOLOGS AND DERIVATIVES

Referring now to Reaction Scheme 2 another general process for synthesizing dihydrobenzofuran-5-yl derivatives of the invention is disclosed. The starting compound in this process is the dihydro-5-aminobenzofurane derivative of Formula 8 which can be obtained as disclosed in connection with Reaction Scheme 1. When it is desired to introduce into the molecule an $R_1$ group of the type where the carbon adjacent to the nitrogen is secondary, then the dihydro-5-aminobenzofurane derivative of Formula 8 is reacted in a reductive alkylation reaction with a ketone compound of the formula $(R^*_1)_2CO$ where the symbol $R^*_1$ is defined such that the radical $(R^*_1)_2CH-$ is within the definition of $R_1$. Acetone is an example for the ketone compound of the formula $(R^*_1)_2CO$, and results in the introduction of an iso-propyl group to the amino nitrogen of the compound of Formula 8. The reductive alkylation reaction is typically conducted in an alcoholic solvent (ethanol), in the presence of sodium borohydride, sodium acetate and acetic acid. The resulting secondary amine of Formula 12 is thereafter reacted with the halogenated reagent of Formula 9 as is described in connection with Reaction Scheme 1, that is in the presence of the catalysts tris(dibenzylideneacetone)dipalladium(0) $(Pd_2(dba)_3)$, and (S)-(−)-2,2′-bis(diphenylphosphino)1,1′-binaphthyl (BINAP), an acid acceptor, such as cesium carbonate, while heated in an inert solvent (toluene) in an inert gas atmosphere. As noted above, the resulting tertiary amine compounds having an aryl or heteroaryl Y group as one substituent, the dihydrobenzofuran-5-yl group as the second substituent and the $R_1$ group as the third substituent are preferably prepared through the intermediate compound of Formula 12 when the carbon of $R_1$ adjacent to the amino nitrogen is a secondary carbon, although this particular synthetic route is applicable to other $R_1$ groups as well.

Reaction Scheme 2 also discloses an alternative synthetic route wherein the dihydro-5-aminobenzofurane derivative of Formula 8 is first reacted with the halogenated reagent of Formula 9 as is described above, and the resulting dihydrobenzofuran-5-yl and aryl or heteroaryl substituted secondary amine of Formula 14 is subjected to a reductive alkylation reaction with an aldehyde of the formula $R^*_1$—CHO where the group $R_1^*$— is defined to the extent it can be made applicable, as the group $R_1$ in Formula 1 with one less $CH_2$ unit, that is a homolog having one $CH_2$ unit (carbon atom) less than the group $R_1$. The reductive alkylation reaction is typically conducted with the aldehyde in the presence of sodium cyanoborohydride, and acetic acid, usually in acetonitrile as the solvent. The reductive alkylation reaction provides the tertiary amine compounds of Formula 13 within the scope of the invention, and which can be converted into further homologs and derivatives as described above in connection with Reaction Scheme 1.

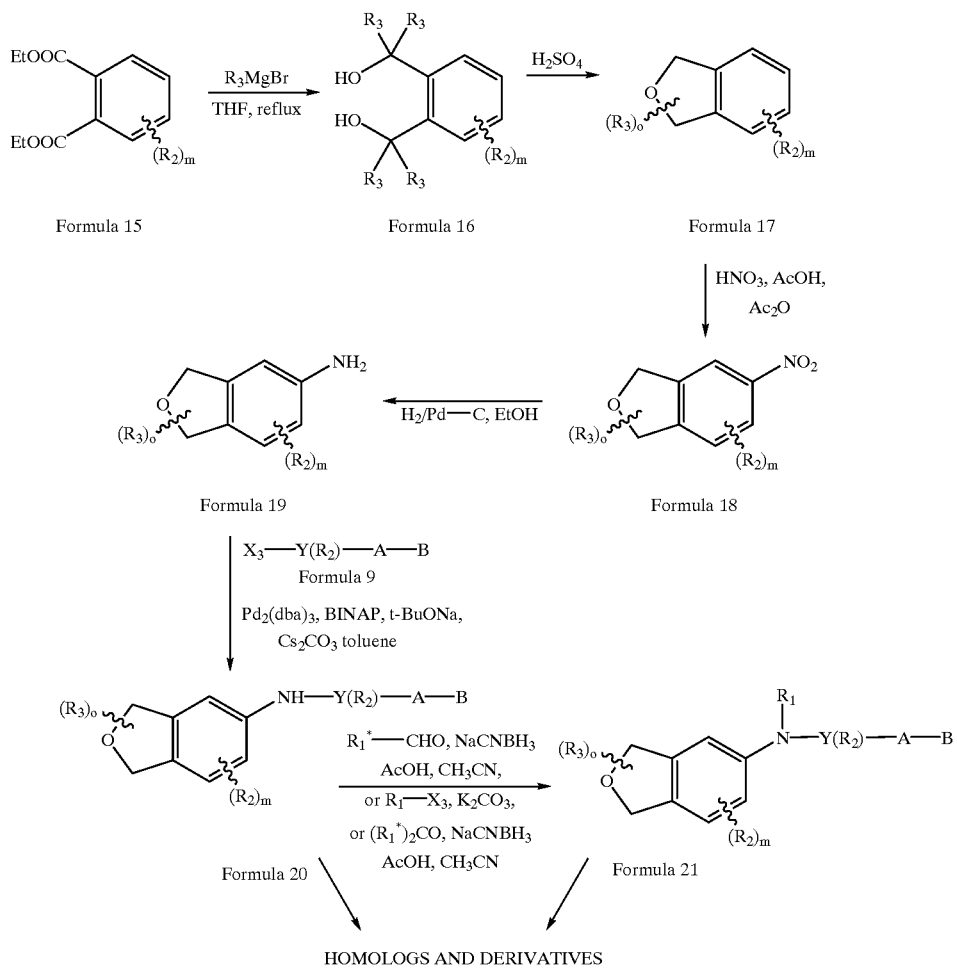

REACTION SCHEME 3

Reaction Scheme 3 discloses a synthetic route for the preparation of the isobenzofuran compounds of Formula 2. In accordance with this scheme, diethyl phthalate, or a derivative of diethyl phthalate of Formula 15 where the benzene ring is already substituted with one or more $R_2$ groups, is reacted with a Grignard reagent of the formula $R_3MgBr$ (or like organometal reagent) to provide the dihydroxy derivative of Formula 16. The starting compound diethyl phthalate is commercially available, while the derivatives of Formula 15 can, generally speaking, be obtained in accordance with the chemical scientific and patent literature, or by such modifications of the published literature procedures which will become readily apparent to the practicing synthetic organic chemist. The dihydroxy derivatives of Formula 16 are then ring closed by treatment with acid (typically 60% sulfuric acid) to provide the 1,3-dihydro-iso-benzofuran derivative of Formula 17. The above summarized synthesis of the compounds of Formula 17 is conducted substantially in accordance with the procedure described in the publication by Bennett et al. in *J. Chem. Soc.*, 1936, 1114, incorporated herein by reference. Nitration of the 1,3-dihydro-iso-benzofuran derivatives of Formula 17 provides the 1,3-dihydro-4-nitro-iso-benzofuran compounds of Formula 18. The nitro compounds of Formula 18 are reduced with hydrogen on a suitable catalyst, such as palladium, to give the 1,3-dihydro-4-amino-iso-benzofuran compounds of Formula 19.

Reaction of the 1,3-dihydro-4-amino-iso-benzofuran compounds of Formula 19 with the halogenated reagent of Formula 9, as is described above, provides the aryl or heteroaryl and 1,3-dihydro-iso-benzofuran-4-yl substituted secondary amine compounds of Formula 20. The compounds of Formula 20 are within the scope of the invention and can be converted to further secondary amine homologs and derivatives. Preferably, the secondary amines of Formula 20 are converted to the tertiary amines of Formula 21, by reductive alkylation with an aldehyde of the formula $R^*_1$—CHO, or with an alkylating agent of the formula $R_1$—$X_3$ as is shown in the scheme and is described above in connection with Reaction Schemes 1 and 2, respectively. The group $R_1^*$— is defined to the extent it can be made applicable, as the group $R_1$ in Formula 1 with one less $CH_2$ unit, that is a homolog having one $CH_2$ unit (carbon atom) less than the group $R_1$. Alternatively, the secondary amine of Formula 20 can also be reacted in a reductive alkylation reaction with a ketone compound of the formula $(R^*_1)_2CO$ where the symbol $R^*_1$ is defined such that the radical $(R^*_1)_2CH$— is within the definition of $R_1$. As it is described in connection with Reaction Scheme 2, this reagent is used when it is desired to introduce into the molecule an $R_1$ group of the type where the carbon adjacent to the nitrogen is secondary. The $R_1$, 1,3-dihydro-iso-benzofuran-5-yl, and aryl or heteroaryl substituted tertiary amine compound of Formula 21 is within the scope of the invention and can be converted into further homologs and derivatives, as described above.

SPECIFIC EMBODIMENTS

With reference to the symbol Y in Formulas 1 and 2, the preferred compounds of the invention are those where Y is phenyl, naphthyl, pyridyl, thienyl or furyl. Even more preferred are compounds where Y is phenyl. As far as substitutions on the Y (phenyl) and Y (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention there is no $R_2$ substituent on the Y group.

The A—B group of the preferred compounds is $(CH_2)_q COOH$ or $(CH_2)_q$—$COOR_8$, where $R_8$ is defined as above. Even more preferably q is zero and $R_8$ is lower alkyl or the compound is a carboxylic acid, or a pharmaceutically acceptable salt thereof In some other preferred compounds of the invention q is zero and B represents an OH group.

$R_1$ is preferably an alkyl group, Among the alkyl groups methyl, ethyl, n-propyl, iso-propyl, n-butyl and iso-butyl and other branched-chain alkyl groups are preferred. In this regard it should be noted that in the definition of this invention the term alkyl includes cycloalkyl and cycloalkylalkyl groups.

$R_2$ attached to the aromatic portion of the dihydrobenzofuran or dihydro-iso-benzofuran nucleus is preferably hydrogen or lower alkyl, more preferably hydrogen, methyl, ethyl, iso-propyl and t-butyl.

The $R_3$ substituents preferably are H or lower alkyl, even more preferably H or methyl. Still more preferably the symbol $(R_3)_o$ represents geminal dimethyl groups disposed in the 3-position of the dihydrobenzofuran and both in the 1 and 3 positions of the dihydro-iso-benzofuran nucleus.

The most preferred compounds of the invention are disclosed in Table 2 with reference to Formulas 22 and 23.

Formula 22

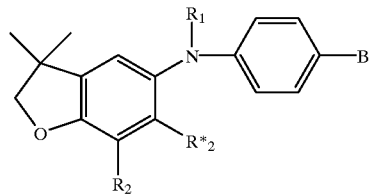

Formula 23

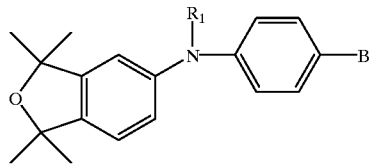

| Compound No. | Formula | $R_1$ | $R_2$ | $R_2^*$ | B |
|---|---|---|---|---|---|
| 15 | 22 | H | $CH_3$ | H | COOEt |
| 16 | 22 | H | Et | H | COOEt |
| 17 | 22 | H | i-propyl | H | COOEt |
| 18 | 22 | H | t-butyl | H | COOEt |
| 19 | 22 | $CH_3$ | $CH_3$ | H | COOEt |
| 20 | 22 | Et | $CH_3$ | H | COOEt |
| 26 | 22 | $CH_3$ | $CH_3$ | H | COOH |
| 27 | 22 | Et | $CH_3$ | H | COOH |
| 37 | 22 | i-propyl | $CH_3$ | H | COOEt |
| 41 | 22 | i-propyl | $CH_3$ | H | COOH |
| 23 | 22 | $CH_3$ | i-propyl | H | COOEt |
| 30 | 22 | $CH_3$ | i-propyl | H | COOH |
| 24 | 22 | Et | i-propyl | H | COOEt |
| 31 | 22 | Et | i-propyl | H | COOH |
| 25 | 22 | Et | t-butyl | H | COOEt |
| 32 | 22 | Et | t-butyl | H | COOH |
| 40 | 22 | i-propyl | t-butyl | H | COOEt |
| 44 | 22 | i-propyl | t-butyl | H | COOH |
| 39 | 22 | i-propyl | i-propyl | H | COOEt |
| 43 | 22 | i-propyl | i-propyl | H | COOH |
| 21 | 22 | $CH_3$ | ethyl | H | COOEt |
| 28 | 22 | $CH_3$ | ethyl | H | COOH |
| 22 | 22 | ethyl | ethyl | H | COOEt |
| 29 | 22 | ethyl | ethyl | H | COOH |

-continued

| Compound No. | Formula | $R_1$ | $R_2$ | $R_2*$ | B |
|---|---|---|---|---|---|
| 38 | 22 | i-propyl | ethyl | H | COOEt |
| 42 | 22 | i-propyl | ethyl | H | COOH |
| 57 | 22 | i-propyl | t-butyl | $CH_3$ | $OCH_3$ |
| 61 | 22 | i-propyl | t-butyl | $CH_3$ | OH |
| 69 | 22 | i-propyl | t-butyl | $CH_3$ | COOMe |
| 73 | 22 | i-propyl | t-butyl | $CH_3$ | COOH |
| 56 | 22 | ethyl | t-butyl | $CH_3$ | $OCH_3$ |
| 60 | 22 | ethyl | t-butyl | $CH_3$ | OH |
| 68 | 22 | ethyl | t-butyl | $CH_3$ | COOMe |
| 72 | 22 | ethyl | t-butyl | $CH_3$ | COOH |
| 55 | 22 | i-propyl | i-propyl | $CH_3$ | $OCH_3$ |
| 59 | 22 | i-propyl | i-propyl | $CH_3$ | OH |
| 67 | 22 | i-propyl | i-propyl | $CH_3$ | COOMe |
| 71 | 22 | i-propyl | i-propyl | $CH_3$ | COOH |

-continued

| Compound No. | Formula | $R_1$ | $R_2$ | $R_2*$ | B |
|---|---|---|---|---|---|
| 54 | 22 | ethyl | i-propyl | $CH_3$ | $OCH_3$ |
| 58 | 22 | ethyl | i-propyl | $CH_3$ | OH |
| 66 | 22 | ethyl | i-propyl | $CH_3$ | $COOCH_3$ |
| 70 | 22 | ethyl | i-propyl | $CH_3$ | COOH |
| 79 | 23 | H | — | — | COOEt |
| 80 | 23 | ethyl | — | — | COOEt |
| 83 | 23 | ethyl | — | — | COOH |
| 81 | 23 | n-propyl | — | — | COOEt |
| 84 | 23 | n-propyl | — | — | COOH |
| 82 | 23 | n-butyl | — | — | COOEt |
| 85 | 23 | n-butyl | — | — | COOH |
| 86 | 23 | i-propyl | — | — | COOEt |
| 87 | 23 | i-propyl | — | — | COOH |

REACTION SCHEME 4

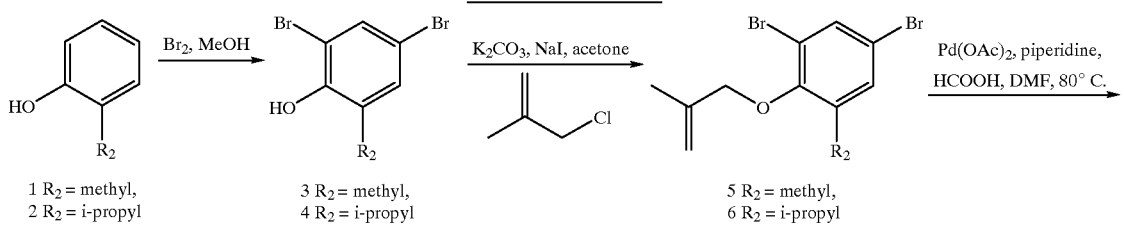

1 $R_2$ = methyl,
2 $R_2$ = i-propyl

3 $R_2$ = methyl,
4 $R_2$ = i-propyl

5 $R_2$ = methyl,
6 $R_2$ = i-propyl

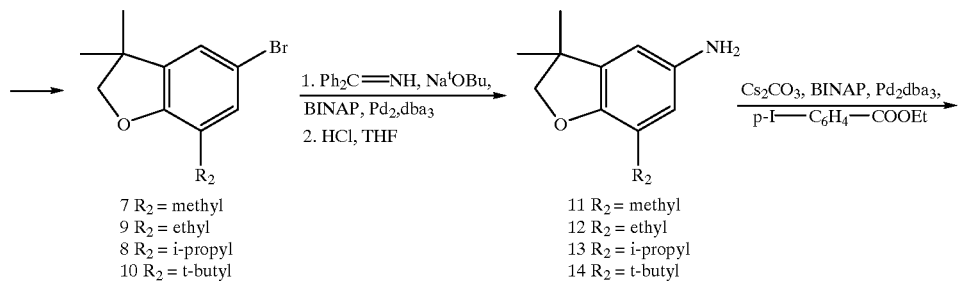

7 $R_2$ = methyl
9 $R_2$ = ethyl
8 $R_2$ = i-propyl
10 $R_2$ = t-butyl

11 $R_2$ = methyl
12 $R_2$ = ethyl
13 $R_2$ = i-propyl
14 $R_2$ = t-butyl

J. Med. Chem., 1998, 41, 1124–1137

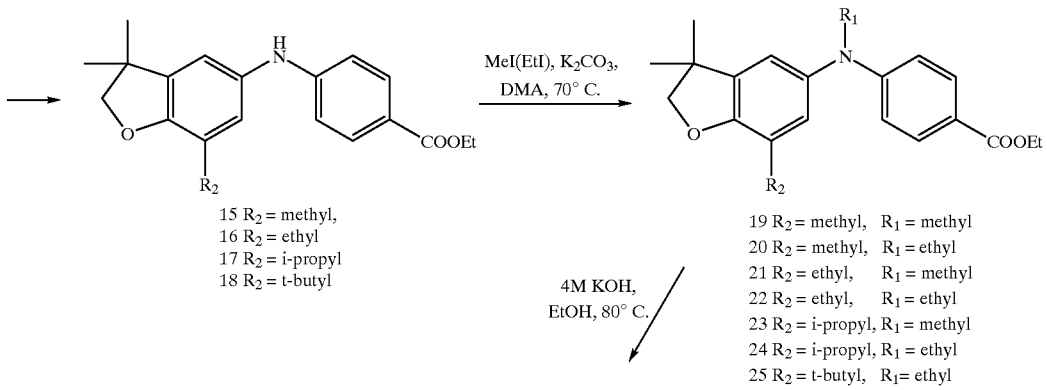

15 $R_2$ = methyl,
16 $R_2$ = ethyl
17 $R_2$ = i-propyl
18 $R_2$ = t-butyl

19 $R_2$ = methyl, $R_1$ = methyl
20 $R_2$ = methyl, $R_1$ = ethyl
21 $R_2$ = ethyl, $R_1$ = methyl
22 $R_2$ = ethyl, $R_1$ = ethyl
23 $R_2$ = i-propyl, $R_1$ = methyl
24 $R_2$ = i-propyl, $R_1$ = ethyl
25 $R_2$ = t-butyl, $R_1$ = ethyl 4M KOH, EtOH, 80° C.

-continued

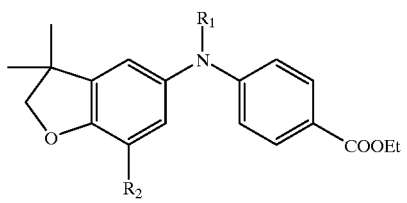

26 $R_2$ = methyl, $R_1$ = methyl
27 $R_2$ = methyl, $R_1$ = ethyl
28 $R_2$ = ethyl, $R_1$ = methyl
29 $R_2$ = ethyl, $R_1$ = ethyl
30 $R_2$ = i-propyl, $R_1$ = methyl
31 $R_2$ = i-propyl, $R_1$ = ethyl
32 $R_2$ = t-butyl, $R_1$ = ethyl

REACTION SCHEME 5

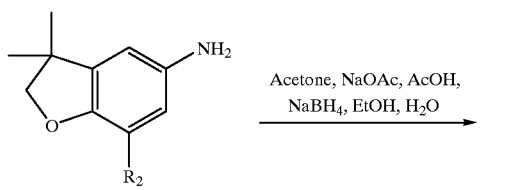

11 $R_2$ = methyl
12 $R_2$ = ethyl
13 $R_2$ = i-propyl
14 $R_2$ = t-butyl

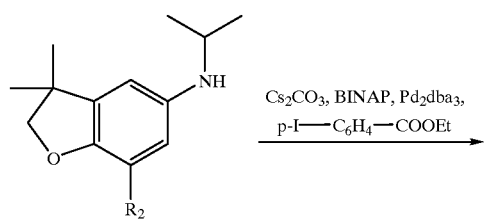

33 $R_2$ = methyl
34 $R_2$ = ethyl
35 $R_2$ = i-propyl
36 $R_2$ = t-butyl

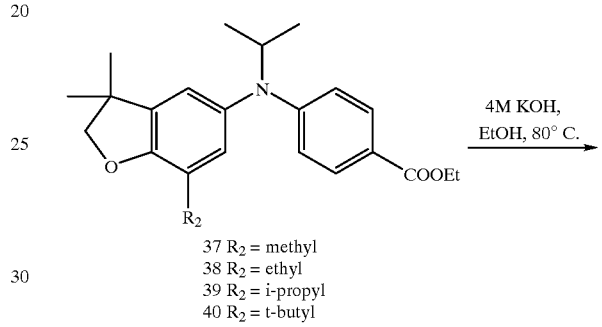

37 $R_2$ = methyl
38 $R_2$ = ethyl
39 $R_2$ = i-propyl
40 $R_2$ = t-butyl

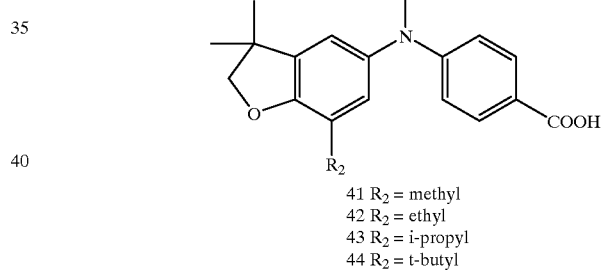

41 $R_2$ = methyl
42 $R_2$ = ethyl
43 $R_2$ = i-propyl
44 $R_2$ = t-butyl

REACTION SCHEME 6

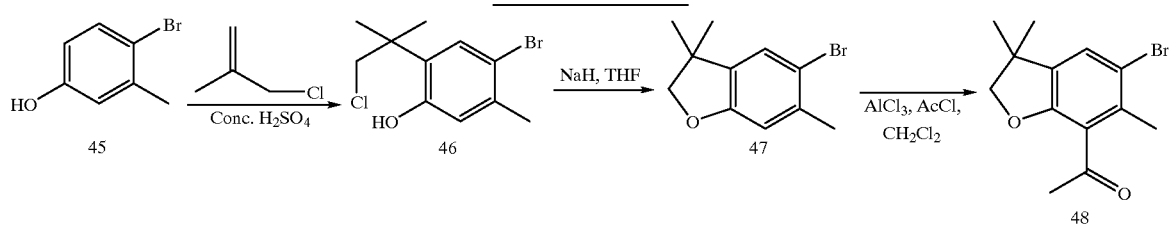

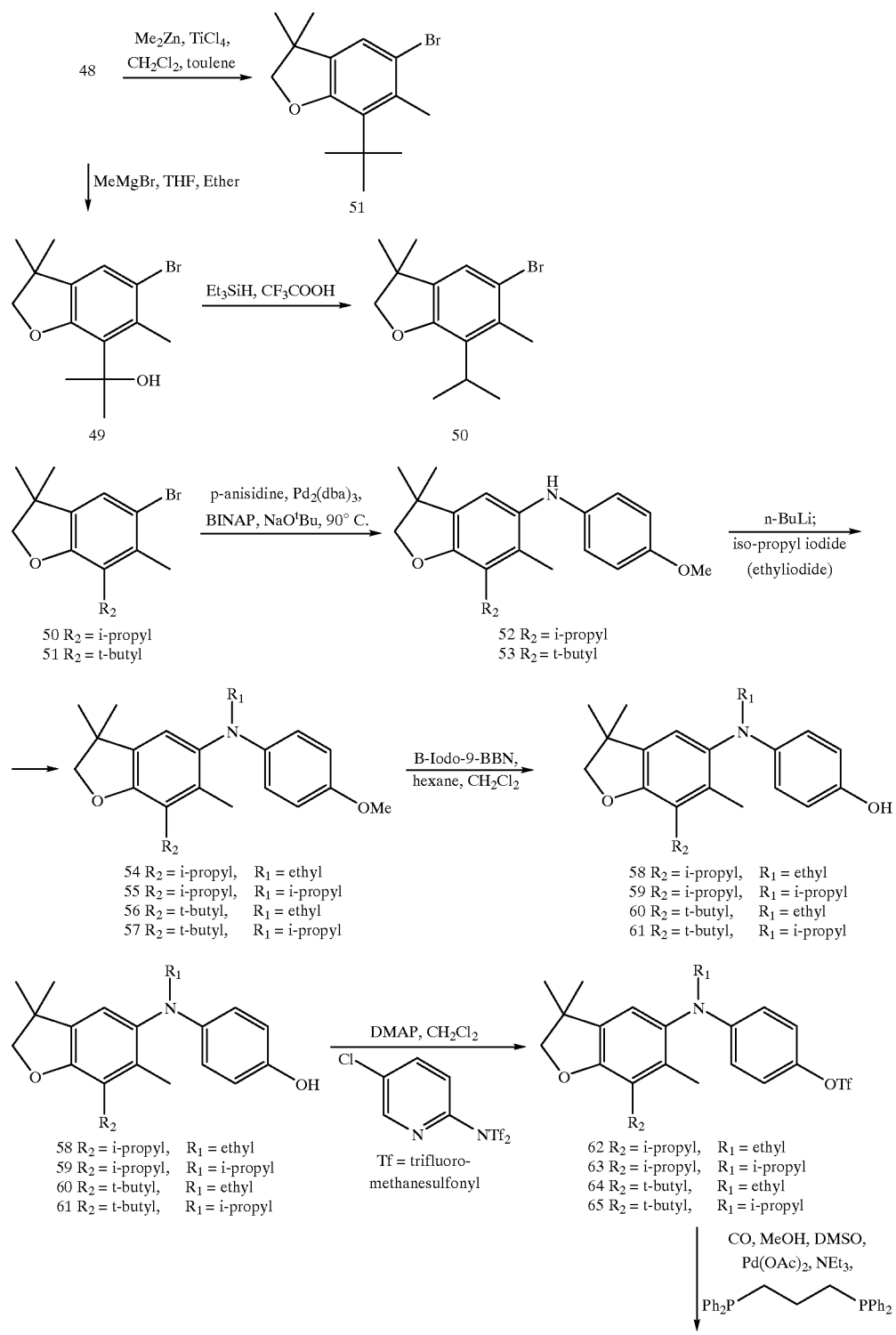

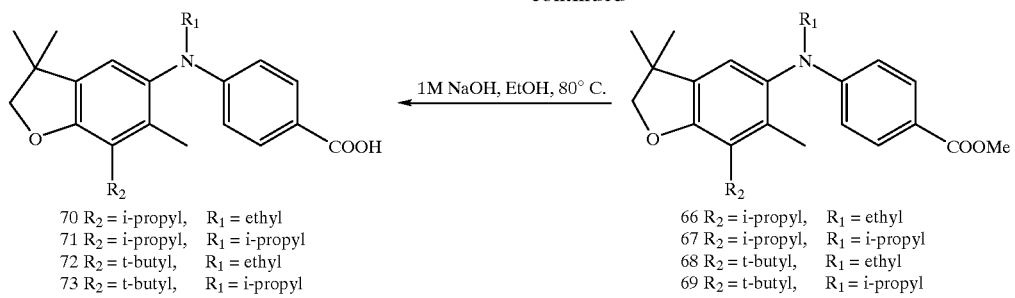

70 R$_2$ = i-propyl, R$_1$ = ethyl
71 R$_2$ = i-propyl, R$_1$ = i-propyl
72 R$_2$ = t-butyl, R$_1$ = ethyl
73 R$_2$ = t-butyl, R$_1$ = i-propyl 66 R$_2$ = i-propyl, R$_1$ = ethyl
67 R$_2$ = i-propyl, R$_1$ = i-propyl
68 R$_2$ = t-butyl, R$_1$ = ethyl
69 R$_2$ = t-butyl, R$_1$ = i-propyl

REACTION SCHEME 7

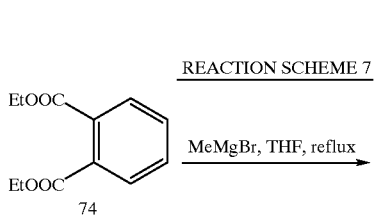
74

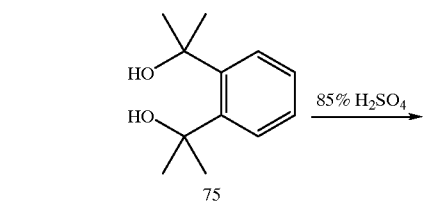
75

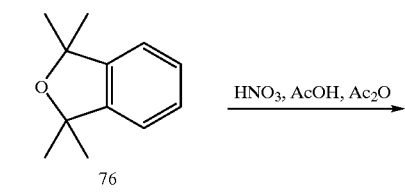
76
J. Chem. Soc., 1936, 1114

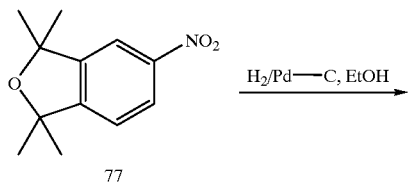
77

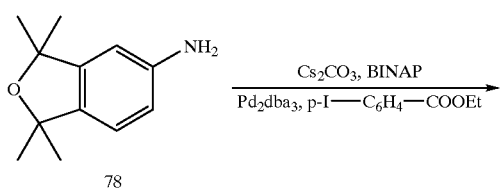
78

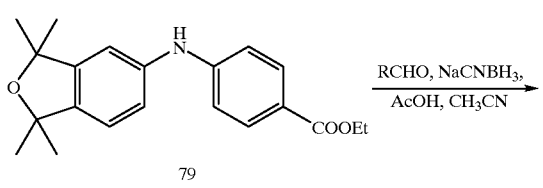
79

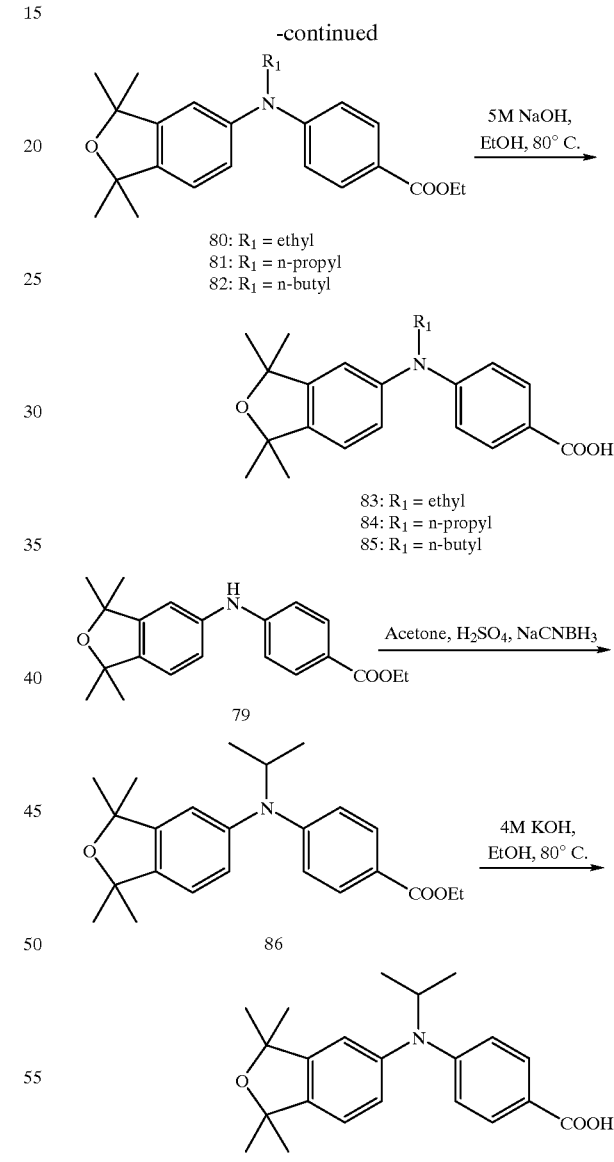

80: R$_1$ = ethyl
81: R$_1$ = n-propyl
82: R$_1$ = n-butyl

83: R$_1$ = ethyl
84: R$_1$ = n-propyl
85: R$_1$ = n-butyl

86

87

Reaction Scheme 4 discloses the presently preferred synthesis of several exemplary compounds of the invention in accordance with Formula 22, where the 6-position of the dihydrobenzofuiran moiety is not substituted and the 7-position has an alkyl substituent and where the third (alkyl) substituent is introduced to the amino nitrogen by an alkylation reaction.

Reaction Scheme 5 discloses the presently preferred synthesis of several exemplary compounds of the invention in accordance with Formula 22, where the third (alkyl) substituent on the amino nitrogen is an iso-propyl group that is introduced by reductive alkylation of a primary amine.

Reaction Scheme 6 discloses the presently preferred synthesis to provide exemplary compounds of Formula 22 where the 6 and 7 positions of the dihydrobenzofuran moiety are both substituted by an alkyl group.

Reaction Scheme 7 discloses the presently preferred synthesis of several exemplary compounds 1,3-dihydro-isobenzofuran compounds of the invention in accordance with Formula 23.

A detailed description of the steps of the processes illustrated in Reaction Schemes 4–7 is provided in the experimental section of this application for patent.

SPECIFIC EXAMPLES 2,4-Dibromo-6-methyl-phenol (Compound 3) General Procedure A:

A cooled (ice-bath) solution of 2-methyl phenol (1) (26.5 g, 0.25 mol) in 70 mL of methanol was treated with bromine (27 mL, 0.525 mol) drop wise over 1 hour. The reaction mixture was allowed to warm to room temperature and stirred for 3 hours. It was then treated with 50 mL of water and the precipitated solid was filtered, washed with water and dried to yield the title compound (62 g, 93%). $^1$H-NMR (300 MHz, CDCl$_3$): δ 7.43(d, 1H, J=2.2 Hz), 7.20(d, 1H, J=1.9 Hz), 5.54(br s, 1H), 2.27(s, 3H).

2,4-Dibromo-6-isopropyl-phenol (Compound 4).

Following general procedure A and using 2-isopropyl-phenol (Compound 2, 34 g, 0.25 mol) in 50 mL of methanol and bromine (28 mL, 0.525 mol), the title compound was obtained as an oil (76.52 g, quantitative yield). $^1$H NMR (300 MHz, CDCl$_3$): δ 7.44 (d, 1H, J=2.2 Hz), 7.25 (d, 1H, J=2.2 Hz), 5.57 (s, 1H), 3.29 (heptet, 1H, J=6.9 Hz), 1.23 (d, 6H, J=6.9 Hz).

1,5-Dibromo-3-methyl-2-(2-methyl-allyloxy)-benzene (Compound 5). General Procedure B:

A solution of 2,4-dibromo-6-methyl-phenol (Compound 3,62 g, 0.23 mol) in 700 mL of acetone was treated with potassium carbonate (38.7 g, 0.28 mol), sodium iodide (3.4 g, 0.023 mol) and 3-chloro-2-methylpropene (34 mL, 0.35 mol) and the resulting suspension was refluxed for 18 hours. The solids were filtered and the filtrate was evaporated in vacuo to afford the title compound as a dark yellow oil. $^1$H-NMR (300 MHz, CDCl$_3$): δ 7.53(d, 1H, J=2.7 Hz), 7.27(d, 1H, J=1.9 Hz), 5.17(s, 1H), 5.02(s, 1H), 4.28(s, 2H), 2.30(s, 3H), 1.92(s, 3H).

1,5-Dibromo-3-isopropyl-2-(2-methyl-allyloxy)-benzene (Compound 6).

Following general procedure B and using 2,4-dibromo-6-isopropyl-phenol (Compound 4, 76.56 g, 0.25 mol), potassium carbonate (41.46 g, 0.3 mol), sodium iodide (3.75 g, 0.025 mol) and 3-chloro-2-methylpropene (74 mL, 0.375 mol) in 1L of acetone, the title compound was obtained as a yellow oil. $^1$H NMR (300 MHz, CDCl$_3$): δ 7.52 (d, 1H, J=2.2 Hz), 7.30 (d, 1H, J=2.2 Hz), 5.17 (s, 1H), 5.01 (s, 1H), 4.29 (s, 2H), 3.29 (heptet, 1H, J=6.9 Hz), 1.91 (s, 3H), 1.23 (d, 6H, J=6.7 Hz).

5-Bromo-3,3,7-trimethyl-2,3-dihydro-benzofuran (Compound 7) General Procedure C:

A solution of 1,5-dibromo-3-methyl-2-(2-methyl-allyloxy)-benzene (Compound 5, 26 g, 81 mmol), triphenylphosphine (1.02 g, 3.9mmol) and palladium(II)acetate (0.9 g, 3.9 mmol) in 600 mL of anhydrous N,N-dimethylformamide was sparged with argon for 5 minutes. To a cooled (ice bath) solution of 7.5 mL of piperidine in 200 ml of N,N-dimethylformamide, 22 mL of 98% formic acid was added and the resulting clear solution was cannulated into the former solution over 0.5 hour and the reaction mixture was heated at 70° C. for overnight. The reaction mixture was cooled to ambient temperature, an equal volume of water was added, and the aqueous layer was extracted with hexanes. The combined organic phases were dried over anhydrous sodium sulfate, filtered and evaporated in vacuo to an oil. The residual oil was diluted with 10 mL of hexanes and washed with 1M sodium hydroxide solution and water, dried over anhydrous sodium sulfate, filtered and evaporated to a residue which was chromatographed using 5% dichloromethane in hexanes to afford the title compound (1.7 g, 8.7%) as a colorless oil; its proton nmr indicated presence of 5% of the debrominated benzofuran. $^1$H-NMR (300 MHz, CDCl$_3$): δ 7.09(d, 1H, J=2.0 Hz), 7.05(d, 1H, J=2.0 Hz), 4.25(s, 2H), 2.20(s, 3H), 1.33(s, 3H).

5-Bromo-3 3-dimethyl-7-isopropyl-2,3-dihydro-benzofuran (Compound 8)

Following general procedure C and using 1,5-dibromo-3-isopropyl-2-(2-methyl-allyloxy)-benzene (Compound 6, 28.45 g, 82 mmol), palladium(II)acetate (0.808 g, 3.5 mmol), triphenyl phosphine (1.02 g, 3.5 mmol), 7.7 mL of piperidine and 21 mL of 98% formic acid in a total volume of 1L of anhydrous N,N-dimethylformamide, the title compound was obtained as a colorless oil (1.6 g, 7.3%). $^1$H NMR (300 MHz, CDCl$_3$): δ 7.12 (d, 1H, J=2.2 Hz), 7.03 (d, 1H, J=2.2 Hz), 4.21 (s, 2H), 3.06 (heptet, 1H, J=6.9 Hz), 1.32 (s, 6H), 1.22 (d, 6H, J=6.9 Hz).

5-Amino-3,3,7-trimethyl-2,3-dihydro-benzofuran (Compound 11) General Procedure D:

A solution of 5-bromo-3,3,7-trimethyl-2,3-dihydro-benzofuran (Compound 7, 0.6 g, 2.5 mmol), benzophenone imine (0.54 g, 3 mmol), sodium-tert-butoxide (0.34 g, 3.5 mmol), tris(dibenzylideneacetone)dipalladium(0) (0.014 g, 0.01 5 mmol) and (S)-(–)-2,2'-bis(diphenylphosphino)-1,1'-binaphthyl (0.029 g, 0.047 mmol) in 10mL of anhydrous toluene was sparged with argon and heated at 80° C. for overnight. The reaction mixture was cooled to ambient temperature, diluted with diethyl ether and filtered. The filtrate was evaporated in vacuo and the residue was dissolved in 7 mL of tetrahydrofiran and treated with 1 mL of 2M hydrochloric acid, and stirred at ambient temperature for 0.5 hour. The volatiles were removed by distillation in vacuo and the residue was dissolved in 0.5M hydrochloric acid and washed with 1:1 hexanes: ethyl acetate. The aqueous phase was neutralized with saturated sodium bicarbonate solution and extracted with dichloromethane. The combined organic extracts were dried over anhydrous sodium sulfate, filtered and evaporated to afford the title compound as a dark brown oil (0.16 g, 36%). $^1$H-NMR (300 MHz, CDCl$_3$): δ 6.33 (s, 2H), 4.18(s, 2H), 2.16(s, 3H), 1.30(s, 3H).

5-Amino-3,3-dimethyl-7-ethyl-2,3-dihydro-benzofuran (Compound 12)

Following general procedure D and using 5-bromo-3,3-dimethyl-7-ethyl-2,3-dihydro-benzofuran (Compound 9, 1.2 g, 4.72 mmol obtained substantially in accordance with *J Med. Chem.* 1998, 41, 1124–1137), benzophenone imine (0.94 g, 5.2 mmol), sodium-tert-butoxide (0.63 g, 6.6 mmol), tris(dibenzylideneacetone)dipalladium(0) (0.020 g, 0.021 mmol) and (S)-(–)-2,2'-bis(diphenylphosphino)-1,1'-binaphthyl (0.040 g, 0.064 mmol) in 10 mL of anhydrous toluene, followed by hydrolysis of the intermediary imine with 2M hydrochloric acid in tetrahydrofuran, the title compound was obtained as an oil (0.7 g, 78%). $^1$H NMR (300 MHz, CDCl$_3$): δ 6.37 (d, 1H, J=2.3 Hz), 6.35 (d, 1H, J=2.3 Hz), 4.17 (s, 2H), 3.15 (br s, 2H), 2.54 (q, 2H, J=7.6 Hz), 1.30 (s, 6H), 1.20 (t, 3H, J=7.6 Hz).

5-Amino-3,3-dimethyl-7-isopropyl-2,3-dihydro-benzofuran (Compound 13)

Following general procedure D and using 5-bromo-3,3-dimethyl-7-isopropyl-2,3-dihydro-benzofuran (Compound 8, 0.268 g, 1 mmol), benzophenone imine (0.199 g, 1.1 mmol), sodium-tert-butoxide (0.134 g, 1.4 mmol), tris(dibenzylideneacetone)dipalladium(0) (0.020 g, 0.021 mmol) and (S)-(−)-2,2'-bis(diphenylphosphino)-1,1'-binaphthyl (0.040 g, 0.064 mmol) in 5 mL of anhydrous toluene, followed by hydrolysis of the intermediary imine with 2M hydrochloric acid in tetrahydrofuran, the title compound was obtained as an oil (0.131 g, 69%). $^1$H NMR (300 MHz, CDCl$_3$): δ 6.39 (d, 1H, J=2.3 Hz), 6.33 (d, 1H, J=2.3 Hz), 4.15 (s, 2H), 3.32 (br s, 2H), 3.03 (heptet, 1H, J=6.9 Hz), 1.28 (s, 6H), 1.22 (d, 6H, J=6.9 Hz).

5-Amino-7-t-butyl-3,3-dimethyl-2,3-dihydro-benzofuran (Compound 14)

Following general procedure D and using 5-bromo-7-t-butyl-3,3-dimethyl-2,3-dihydro-benzofuran (Compound 10, see *J. Med. Chem.* 1998, 41, 1124–1137; 2.0 g, 5.5 mmol), benzophenone imine (1.2 g, 6.64 mmol), sodium-tert-butoxide (0.74 g, 7.75 mmol), tris(dibenzylideneacetone)dipalladium(0) (0.025 g, 0.026 mmol) and (S)-(−)-2,2'-bis(diphenylphosphino)-1,1'-binaphthyl (0.050 g, 0.078 mmol) in 10 mL of anhydrous toluene, followed by hydrolysis of the intermediary imine with 2M hydrochloric acid in tetrahydrofuran, the title compound was obtained as an oil (0.95 g, 72%). $^1$H NMR (300 MHz, CDCl$_3$): δ 6.49 (d, 1H, J=2.4 Hz), 6.39 (d, 1H, J=2.4 Hz), 4.17 (s, 2H), 3.38 (br s, 2H), 1.37 (s, 9H), 1.32 (s, 6H).

4-[(3,3,7-Trimethyl-2,3-dihydro-benzofuran-5-yl)-amino]-benzoic acid ethyl ester (Compound 15) General Procedure E:

A solution of 5-amino-3,3,7-trimethyl-2,3-dihydrobenzofuran (Compound 11), 0.092 g, 0.52 mmol), ethyl-4-iodo-benzoate (0.15 g, 0.57 mmol), cesium carbonate (0.4 g, 0.72 mmol), tris(dibenzylideneacetone)dipalladium(0) (0.015 g, 0.015 mmol) and (S)-(−)-2,2'-bis(diphenylphosphino)-1,1'-binaphthyl (0.029 g, 0.047 mmol) in 3 mL of anhydrous toluene was sparged with argon and heated at 100° C. for 48 hours. After cooling to ambient temperature, the reaction mixture was diluted with diethylether and filtered. The filtrate was evaporated to a brown oil which was subjected to flash column chromatography on silica gel (230–400 mesh) using 12% ethyl acetate in hexanes as the eluent to provide the title compound (0.064 g, 38%) and some recovered starting material. $^1$H NMR (300 MHz, CDCl$_3$): δ 7.89 (d, 2H, J=8.5 Hz), 6.80(s, 2H), 6.79(d, 2H, J=8.3 Hz), 5.89(s, 1H), 4.33(q, 2H, J=7.1 Hz), 4.27(s, 2H), 2.21(s, 3H), 1.36(t, 3H, J=7.1 Hz), 1.33(s, 6H).

4-[(3,3-Dimethyl-7-ethyl-2,3-dihydro-benzofuran-5-yl)-amino]-benzoic acid ethyl ester (Compound 16)

Following general procedure E and using 5-amino-3,3-dimethyl-7-ethyl-2,3-dihydrobenzofuran (Compound 12, 0.22 g, 1.15 mmol), ethyl-4-iodo-benzoate (0.318 g, 115 mmol), cesium carbonate (0.525 g, 1.61 mmol), tris(dibenzylideneacetone)dipalladium(0) (0.020 g, 0.021 mmol), (S)-(−)-2,2'-bis(diphenylphosphino)-1,1'-binaphthyl (0.040 g, 0.064 mmol) in 5 mL of anhydrous toluene, the title compound (0.3 g, 77%) was obtained as a deep yellow solid. $^1$H NMR (300 MHz, CDCl$_3$): δ 7.88 (d, 2H, J=8.8 Hz), 6.79 (m, 4H), 5.92 (br s, 1H), 4.32 (q, 2H, J=7.2 Hz), 4.25 (s, 2H), 2.59 (q, 2H, J=7.5 Hz), 1.36 (t, 3H, J=7.2 Hz), 1.33 (s, 6H), 1.21 (t, 3H, J=7.5 Hz).

4-[(3,3-Dimethyl-7-isopropyl-2,3-dihydro-benzofuran-5-yl)-amino]-benzoic acid ethyl ester (Compound 17)

Following general procedure E and using 5-amino-3,3-dimethyl-7-isopropyl-2,3-dihydrobenzofuran (Compound 13, 0.085 g, 0.5 mmol), ethyl-4-iodo-benzoate (0.123 g, 0.5 mmol), cesium carbonate (0.228 g, 0.7 mmol), tris(dibenzylideneacetone)dipalladium(0) (0.020 g, 0.021 mmol) and (S)-(−)- 2,2'-bis(diphenylphosphino)-1,1'-binaphthyl (0.040 g, 0.064 mmol) in 2 mL of anhydrous toluene (reacted in a sealed tube), the title compound (0.107 g, 76%) was obtained. $^1$H NMR (300 MHz, CDCl$_3$): δ 7.89(d, 2H, J=8.8 Hz), 6.85 (d, 1H, J=2.0 Hz), 6.80 (d, 1H, J=2.0 Hz), 6.78 (d, 2H, J=8.8 Hz), 5.84 (br s, 1H), 4.32 (q, 2H, J=7.2 Hz), 4.25 (s, 2H), 3.08 (heptet, 1H, J=6.9 Hz), 1.36 (t, 3H, J=7.2 Hz), 1.33 (s, 6H), 1.23 (d, 6H, J=6.9 Hz).

4-[(7-t-Butyl-3,3-dimethyl-2,3-dihydro-benzofuran-5-yl)-amino]-benzoic acid ethyl ester (Compound 18)

Following general procedure E and using 5-amino-7-t-butyl-3,3-dimethyl-2,3-dihydrobenzofuran (Compound 14, 0.14 g, 0.47 mmol), ethyl-4-iodo-benzoate (0.0.13 g, 0.57 mmol), cesium carbonate (0.22 g, 0.66 mmol), tris(dibenzylideneacetone)dipalladium(0) (0.020 g, 0.021 mmol) and (S)-(−)-2,2'-bis(diphenylphosphino)-1,1'-binaphthyl (0.040 g, 0.064 mmol) in 4 mL of anhydrous toluene, the title compound (0.15 g, 86%) was obtained. $^1$H NMR (300 MHz, CDCl$_3$): δ 7.92 (d, 2H, J=8.8 Hz), 6.91(d, 1H, J=2.2 Hz), 6.84(d, 1H, J=2.2 Hz), 6.82(d, 1H, J=8.7 Hz), 6.04 (br s, 1H), 4.34 (q, 2H, J=7.1 Hz), 4.26 (s, 2H), 1.36 (s, 9H), 1.33 (s, 6H), 1.29–1.34(buried t, 3H).

4-[Methyl-(3,3,7-trimethyl-2,3-dihydro-benzofuran-5-yl)-amino]-benzoic acid ethyl ester (Compound 19) General Procedure F:

A solution of 4-[(3,3,7-trimethyl-2,3-dihydro-benzofuran-5-yl)-amino]-benzoic acid ethyl ester (Compound 15, 0.016 g, 0.05 mmol) in 1 mL of anhydrous N,N-dimethylacetamide was treated with potassium carbonate (0.07 g, 0.5 mmol) and iodomethane (0.07 g, 0.5 mmol) and heated at 70° C. overnight under argon. The reaction mixture was cooled to ambient temperature, diluted with water and extracted with diethylether. The combined organic extract was dried over anhydrous sodium sulfate, filtered and evaporated to an oil which on flash column chromatography using 10% ethyl acetate in hexanes as the eluent provided the title compound (0.013 g, 77%) as an oil. $^1$H NMR (300 MHz, CDCl$_3$): δ 7.85 (d, 2H, J=8.8 Hz), 6.78 (s, 2H), 6.63 (d, 2H, J=8.8 Hz), 4.32 (q, 2H, J=7.1 Hz), 4.27 (s, 2H), 3.30 (s, 3H), 2.21 (s, 3H), 1.37 (t, 3H, J=7.1 Hz), 1.33(s, 6H).

4-[Ethyl-(3,3,7-trimethyl-2,3-dihydro-benzofuran-5-yl)-amino]-benzoic acid ethyl ester (Compound 20) General Procedure G:

A solution of 4-[(3,3,7-trimethyl-2,3-dihydro-benzofuran-5-yl)-amino]-benzoic acid ethyl ester (Compound 15, 0.053 g, 0.1 6 mmol) in 1.5 mL of anhydrous N,N-dimethylacetamide was treated with potassium carbonate (0.28 g, 2 mmol) and iodomethane (0.35 g, 2 mmol) and heated at 70° C. for 48 hours under argon. The reaction mixture was cooled to ambient temperature, diluted with water and extracted with diethylether. The combined organic extract was dried over anhydrous sodium sulfate, filtered and evaporated to an oil which on flash column chromatography using 10% ethyl acetate in hexanes as the eluent provided the title compound (0.013 g, 30% based on recovered starting material) as an oil. $^1$H NMR (300 MHz, CDCl$_3$): δ 7.82 (d, 2H, J=7.0 Hz), 6.76 (d, 1H, J=2.1 Hz), 6.75 (d, 1H, J=2.1 Hz), 6.57 (d, 2H, J=7.0 Hz), 4.31 (q, 2H, J=7.1 Hz), 4.30 (s, 2H), 3.72 (q, 2H, J=7.1 Hz), 2.21 (s, 3H), 1.35 (t, 3H, J=7.1 Hz), 1.33 (s, 6H), 1.24 (t, 3H, J=7.1 Hz).

4-[Methyl-(3,3-dimethyl-7-ethyl-2,3-dihydro-benzofuran-5-yl)-amino]-benzoic acid ethyl ester (Compound 21)

Following general procedure F and using 4-[(3,3-dimethyl-7-ethyl-2,3-dihydro-benzofuran-5-yl)-amino]-benzoic acid ethyl ester (Compound 16, 0.12 g, 0.35 mmol), potassium carbonate (0.49 g, 3.5 mmol) and iodomethane (0.50 g, 3.5 mmol) in 2 mL of anhydrous N,N-dimethylacetamide, the title compound (0.095 g, 80%) was obtained as a pale yellow oil. $^1$H NMR (300 MHz, CDCl$_3$): δ 7.85 (d, 2H, J=9.1 Hz), 6.81 (d, 1H, J=2.3 Hz), 6.78 (d, 1H, J=2.3 Hz), 6.63 (d, 2H, J=9.1 Hz), 4.31 (q, 2H, J=7.1 Hz), 4.28 (s, 2H), 3.31 (s, 3H), 2.59 (q, 2H,J=7.6 Hz), 1.35 (t, 3H, J=7.1 Hz), 1.33 (s, 6H), 1.22 (t, 3H, J=7.6 Hz).

4-[Ethyl-(3,3-dimethyl-7-ethyl-2,3-dihydro-benzofuran-5-yl)-amino]-benzoic acid ethyl ester (Compound 22)

Following general procedure G and using 4-[(3,3-dimethyl-7-ethyl-2,3-dihydro-benzofuran-5-yl)-amino]-benzoic acid ethyl ester (Compound 16, 0.18 g, 0.53 mmol), potassium carbonate (0.73 g, 5.3 mmol) and iodomethane (0.83 g, 5.3 mmol) in 2 mL of anhydrous N,N-dimethylacetamide, the title compound (0.134 g, 68%) was obtained as a pale yellow oil. The reaction was performed in a sealed tube. $^1$H NMR (300 MHz, CDCl$_3$): δ 7.82 (d, 2H, J=9.0 Hz), 6.79 (d, 1H, J=2.0 Hz), 6.76 (d, 1H, J=2.0 Hz), 6.57 (d, 2H, J=9.0 Hz), 4.31 (q, 2H, J=7.1 Hz), 4.27 (s, 2H), 3.72 (q, 2H, J=7.1 Hz), 2.60 (q, 2H J=7.6 Hz), 1.35 (t, 3H, J=7.1 Hz), 1.33 (s, 6H), 1.26–1.19 (m, 6H).

4-[Methyl-(3,3-dimethyl-7-isopropyl-2,3-dihydro-benzofuran-5-yl)-amino]-benzoic acid ethyl ester (Compound 23).

Following general procedure F and using 4-[(3,3-dimethyl-7-isopropyl-2,3-dihydro-benzofuran-5-yl)-amino]-benzoic acid ethyl ester (Compound 17, 0.043 g, 0.127 mmol), potassium carbonate (0.139 g, 1 mmol) and iodomethane (0.144 g, 1 mmol) in 1 mL of anhydrous N,N-dimethylacetamide, the title compound (0.031 g, 70%) was obtained as a pale yellow oil. $^1$H NMR (300 MHz, CDCl$_3$): δ 7.78 (d, 2H, J=9.0 Hz), 6.77 (d, 1H, J=2.1 Hz), 6.70 (d, 1H, J=2.1 Hz), 6.55 (d, 2H, J=9.0 Hz), 4.24 (q, 2H, J=7.1 Hz), 4.20 (s, 2H), 3.24 (s, 3H), 3.01 (heptet, 1H, J=7.0 Hz), 1.28 (t, 3H, J=7.1 Hz), 1.25 (s, 6H), 1.15 (d, 6H, J=7.0 Hz).

4-[Ethyl-(3,3-dimethyl-7-isopropyl-2,3-dihydro-benzofuran-5-yl)-amino]-benzoic acid ethyl ester (Compound 24)

Following general procedure G and using 4-[(3,3-dimethyl-7-isopropyl- 2,3-dihydro-benzofuran-5-yl)-amino]-benzoic acid ethyl ester (Compound 17, 0.064 g, 0.19 mmol), potassium carbonate (0.105×2 g, 0.76×2 mmol) and iodomethane (0.24×2 g, 0.76×2 mmol) in 2 mL of anhydrous N,N-dimethylacetamide, the title compound (0.05 g, 75%) was obtained as a pale yellow oil. This reaction was performed in a sealed tube for 96 hours, with addition of a second equivalent of potassium carbonate and iodomethane to the reaction mixture after 48 hours. $^1$H NMR (300 MHz, CDCl$_3$): δ 7.75 (d, 2H, J=9.0 Hz), 6.74 (d, 1H, J=2.1 Hz), 6.67 (d, 1H, J=2.1 Hz), 6.49 (d, 2H, J=9.0 Hz), 4.23 (q, 2H, J=7.1 Hz), 4.20 (s, 2H), 3.66 (q, 2H, J=7.1 Hz), 3.01 (heptet, 1H J=6.8 Hz), 1.27 (t, 3H, J=7.1 Hz), 1.25 (s, 6H), 1.19–1.13 (m, 9H).

4-[Ethyl-(7-t-butyl-3,3-dimethyl-2,3-dihydro-benzofuran-5-yl)-amino]-benzoic acid ethyl ester (Compound 25)

Following general procedure G and using 4-[(7-t-butyl-3,3-dimethyl-2,3-dihydro-benzofuran-5-yl)-amino]-benzoic acid ethyl ester (Compound 18, 0.15 g, 0.41 mmol), potassium carbonate (1.65 g, 12 mmol) and iodomethane (0.94 g, 6 mmol) in 5 mL of anhydrous N,N-dimethylacetamide, the title compound (0.090 g, 56%) was obtained as a pale yellow oil. $^1$H NMR (300 MHz, CDCl$_3$): δ 7.85 (d, 2H, J=8.9 Hz), 6.87 (d, 1H, J=2.2 Hz), 6.77 (d, 1H, J=2.2 Hz), 6.57 (d, 2H, J=9.1 Hz), 4.29 (q, 2H, J=7.1 Hz), 4.28 (s, 2H), 3.74 (q, 2H, J=7.0 Hz), 1.36 (t, 3H, J=7.1 Hz), 1.36 (s, 9H), 1.33(s, 6H), 1.26 (t, 3H, J=7.1 Hz)).

4-[Methyl-(3,3,7-trimethyl-2,3-dihydro-benzofuran-5-yl)-amino]-benzoic acid (Compound 26) General Procedure H:

A solution of 4-[methyl-(3,3,7-trimethyl-2,3-dihydro-benzofuran-5-yl)-amino]-benzoic acid ethyl ester (Compound 19, 0.013 g, 0.037 mmol) in 1.1 mL of ethanol was treated with 4M potassium hydroxide solution (1 mL, 4 mmol) and the resulting clear solution was heated at 80° C. for 2 hours. The volatiles were removed by distillation in vacuo, the residue was neutralized with dilute hydrochloric acid and extracted with dichloromethane. The organic extract was dried over anhydrous sodium sulfate, filtered and evaporated to afford the title compound (0.010 g, 84%) as pale yellow solid. $^1$H NMR (300 MHz, CDCl$_3$): δ 7.91 (d, 2H, J=9.1 Hz), 6.80(s, 1H), 6.79(s, 1H), 6.65(d, 2H, J=9.1 Hz), 4.29(s, 2H), 3.32 (s, 3H), 2.21(s, 3H), 1.34(s, 6H).

4-[Ethyl-(3,3,7-trimethyl-2,3-dihydro-benzofuran-5-yl)-amino]-benzoic acid (Compound 27).

Following general procedure G and using 4-[ethyl-(3,3,7-trimethyl-2,3-dihydro-benzofuran-5-yl)-amino]-benzoic acid ethyl ester (Compound 20, 0.013 g, 0.37 mmol) and 1 mL (4 mmol) of 4M potassium hydroxide solution in 1.1 mL of ethanol, the title compound (0.009 g, 75%) was obtained as a solid. $^1$H NMR (300 MHz, CDCl$_3$): δ 7.86 (d, 2H, J=9.0 Hz), 6.77 (s, 1H), 6.75 (s, 1H), 6.57 (d, 2H, J=9.0 Hz), 4.29 (s, 2H), 3.72 (q, 2H, J=7.1 Hz), 2.21 (s, 3H), 1.33 (s, 6H), 1.25 (t, 3H, J=7.1 Hz).

4-[Methyl-(7-ethyl-3,3-dimethyl-2,3-dihydro-benzofuran-5-yl)-amino]-benzoic acid (Compound 28) General Procedure I:

A solution of 4-[methyl-(7-ethyl-3,3-dimethyl-2,3-dihydro-benzofuran-5-yl)-amino]-benzoic acid ethyl ester (Compound 21, 0.095 g, 0.27 mmol) in 10 mL of ethanol was treated with 2 mL (10 mmol) of 5M sodium hydroxide solution and the reaction mixture was stirred overnight at room temperature, and at 55° C. for 2 hours. The volatiles were removed by distillation in vacuo and the residue was neutralized with dilute hydrochloric acid, and extracted with ethyl acetate. The organic extract was washed with brine and dried over anhydrous sodium sulfate, filtered and evaporated to afford the title compound (0.070 g, 80%) as a white solid. $^1$H NMR (300 MHz, CDCl$_3$): δ 7.92 (d, 2H, J=9.0 Hz), 6.83 (d, 1H, J=2.1 Hz), 6.80 (d, 1H, J=2.1 Hz), 6.65 (d, 2H, J=9.0 Hz), 4.30 (s, 2H), 3.34 (s, 3H), 2.64 (q, 2H, J=7.6 Hz), 1.35(s, 6H), 1.23 (t, 3H, J=7.6 Hz).

4-[Ethyl-(3,3-dimethyl-7-ethyl-2,3-dihydro-benzofuran-5-yl)-amino]-benzoic acid (Compound 29)

Following general procedure I and using 4-[ethyl-(3,3-dimethyl-7-ethyl-2,3-dihydro-benzofuran-5-yl)-amino]-benzoic acid ethyl ester (Compound 22, 0.134 g, 0.36 mmol) and 2 mL of 5M sodium hydroxide solution in 2 mL of ethanol, the title compound (0.071 g, 58%) was obtained as a white solid. $^1$H NMR (300 MHz, CDCl$_3$): δ 7.88 (d, 2H, J=9.0 Hz), 6.80 (d, 1H, J=2.0 Hz), 6.76 (d, 1H, J=2.0 Hz), 6.58 (d, 2H, J=9.0 Hz), 4.29 (s, 2H), 3.73 (q, 2H, J=7.1 Hz), 2.60 (q, 2H J=7.5 Hz), 1.34 (s, 6H), 1.27–1.12 (m, 6H).

4-[Methyl-(3,3-dimethyl-7-isopropyl-2,3-dihydro-benzofuran-5-yl)-amino]-benzoic acid (Compound 30)

Following general procedure I and using 4-[methyl-(3,3-dimethyl-7-isopropyl-2,3-dihydro-benzofuran-5-yl)- amino]-benzoic acid ethyl ester (Compound 23, 0.03 g, 0.081 mmol) and 2 mL of 5M potassium hydroxide solution in 10 mL of ethanol, the title compound (0.022 g, 79%) was obtained as a white solid. $^1$H NMR (300 MHz, CDCl$_3$): δ 7.90 (d, 2H, J=9.0 Hz), 6.85 (d, 1H, J=2.2 Hz), 6.78 (d, 1H, J=2.2 Hz), 6.63 (d, 2H, J=9.0 Hz), 4.27 (s, 2H), 3.33 (s, 3H), 3.09 (heptet, 1H, J=6.8 Hz), 1.33 (s, 6H), 1.23 (d, 6H, J=6.8 Hz).

4-[Ethyl-(3,3-dimethyl-7-isopropyl-2,3-dihydro-benzofuran-5-yl)-amino]-benzoic acid (Compound 31)

Following general procedure I and using 4-[ethyl-(3,3-dimethyl-7-isopropyl-2,3-dihydro-benzofuran-5-yl)-amino]-benzoic acid ethyl ester (Compound 24, 0.045 g, 0.117 mmol) and 2 mL of 5M potassium hydroxide solution in 20 mL of ethanol, the title compound (0.038 g, 86%) was obtained as a white solid. $^1$H NMR (300 MHz, CDCl$_3$): δ 7.80 (d, 2H, J=9.0 Hz), 6.74 (d, 1H, J=2.1 Hz), 6.67 (d, 1H, J=2.1 Hz), 6.50 (d, 2H, J=9.0 Hz), 4.21 (s, 2H), 3.66 (q, 2H, J=7.2 Hz), 3.01 (heptet, 1H J=7.0 Hz), 1.26 (s, 6H), 1.18 (t, 3H J=7.2 Hz), 1.16 (d, 6H, J=7.0 Hz).

4-[Ethyl-(7-t-butyl-3,3-dimethyl-2,3-dihydro-benzofuran-5-yl)-amino]-benzoic acid (Compound 32)

Following general procedure H and using 4-[ethyl-(7-t-butyl-3,3-dimethyl-2,3-dihydro-benzofuran-5-yl)-amino]-benzoic acid ethyl ester (Compound 25, 0.09 g, 0.227 mmol) and 2.5 mL of 4M potassium hydroxide solution in 4 mL of ethanol, the title compound (0.065 g, 78%) was obtained as a pale yellow solid. $^1$H NMR (300 MHz, CDCl$_3$): δ 7.89 (d, 2H, J=9.0 Hz), 6.87 (d, 1H, J=2.1 Hz), 6.78 (d, 1H, J=2.1 Hz), 6.58 (d, 2H, J=9.2 Hz), 4.28 (s, 2H), 3.74 (q, 2H, J=7.1 Hz), 1.36 (s, 9H), 1.33(s, 6H), 1.27 (t, 3H, J=7.1 Hz).

5-(Isopropyl)amino-3,3,7-trimethyl-2,3-dihydro-benzofuran (Compound 33) General Procedure J:

A stirred solution of 5-amino-3,3,7-trimethyl-2,3-dihydro-benzofuran (Compound 11, 0.354 g, 2 mmol) in 5 mL of ethanol, 5 mL of water and 1.6 mL (42 mmol) of acetic acid was treated with 5 mL of acetone and sodium acetate (0.68 g, 5 mmol), cooled in an ice bath and treated with small portions of sodium borohydride (0.64 g, 16 mmol) and stirred at room temperature overnight (1–2 hours are sufficient). The reaction mixture was then evaporated in vacuo and the residue was diluted with water, neutralized with sodium hydroxide and extracted with diethylether. The ethereal extract was dried over anhydrous sodium sulfate, filtered and evaporated to a brown oil. Flash column chromatography using 10% ethyl acetate in hexanes as the eluent afforded the title compound (0.43 g, 98%). $^1$H-NMR (300 MHz, CDCl$_3$): δ 6.28 (d, 1H, J=2.7 Hz), 6.26 (d, 1H, J=2.7 Hz), 4.18 (s, 2H), 3.55 (heptet, 1H, J=6.3 Hz), 2.99–3.22 (br s, 1H), 2.18 (s, 3H), 1.30 (s, 6H), 1.20 (d, 6H, J=6.4 Hz).

3,3-Dimethyl-7-ethyl-5-(isopropyl)amino-2,3-dihydro-benzofuran (Compound 34) Following general procedure J and using 5-amino-3,3-dimethyl-7-ethyl-2,3-dihydro-benzofuran (Compound 12, 0.47 g, 2.4 mmol), sodium acetate (0.83 g, 6.1 mmol) and sodium borohydride (2.32 g, 61.47 mmol) in 5 mL of ethanol, 5 mL of water, 10mL of acetone (excess) and acetic acid (2 mL, 51.64 mmol), the title compound (0.45 g, 78%) was obtained as an oil which was purified by flash column chromatography using 5% ethyl acetate in hexanes as the eluent. $^1$H NMR (300 MHz, CDCl$_3$): δ 6.28 (s, 2H), 4.17 (s, 2H), 3.55 (heptet, 1H, J=6.3 Hz), 2.56 (q, 2H, J=7.7 Hz), 1.31 (s, 6H) 1.23–1.19 (m, 9H).

3,3-Dimethyl-7-isopropyl-5-(isopropyl)amino-2,3-dihydro-benzofuran (Compound 35)

Following general procedure J and using 5-amino-3,3-dimethyl-7-isopropyl-2,3-dihydro-benzofuran (Compound 13, 0.296 g, 1.5 mmol), sodium acetate (0.53 g, 3.9 mmol) and sodium borohydride (1.47 g, 25 mmol) in 5 mL of ethanol, 5 mL of water, 5 mL of acetone (excess) and acetic acid (1.25 mL, 32.74 mmol), the title compound (0.21 g, 60%) was obtained as an oil which was purified by flash column chromatography using 5% ethyl acetate in hexanes as the eluent. $^1$H NMR (300 MHz, CDCl$_3$): δ 6.30 (d, 1H, J=2.3 Hz), 6.26 (d, 1H, J=2.3 Hz), 4.14 (s, 2H), 3.54 (heptet, 1H, J=6.3 Hz), 3.03 (heptet, 1H, J=7.0 Hz), 1.29 (s, 6H), 1.22 (d, 6H, J=7.0 Hz), 1.19 (d, 6H, J=6.3 Hz).

7-t-Butyl-3,3-dimethyl-5-(isopropyl)amino-2,3-dihydro-benzofuran (Compound 36)

Following general procedure J and using 5-amino-7-t-butyl-3,3-dimethyl-2,3-dihydro-benzofuran (Compound 14, 0.55 g, 2.5 mmol), sodium acetate (0.85 g, 6.25 mmol) and sodium borohydride (0.76 g, 20 mmol) in 6.5 mL of ethanol, 6.5 mL of water, 5 mL of acetone (excess) and acetic acid (3.15 g, 52.5 mmol), the title compound (0.62 g, 95%) was obtained as an oil which was purified by flash column chromatography using 5% ethyl acetate in hexanes as the eluent. $^1$H NMR (300 MHz, CDCl$_3$): δ 6.40 (d, 1H, J=2.3 Hz), 6.31 (d, 1H, J=2.3 Hz), 4.17 (s, 2H), 3.58 (heptet, 1H, J=6.3 Hz), 3.00–3.25 (br s, 1H), 1.37(s, 9H), 1.33 s, 6H), 1.24 (d, 6H, J=6.2 Hz).

4-[Isopropyl-(3,3,7-trimethyl-2,3-dihydro-benzofuran-5-yl)-amino]-benzoic acid ethyl ester (Compound 37)

Following general procedure E and using 5-(isopropyl)amino-3,3,7-trimethyl-2,3-dihydro-benzofuran (Compound 33, 0.43 g, 1.96 mmol), ethyl-4-iodo-benzoate (0.516 g, 2.4 mmol), cesium carbonate (0.92 g, 2.8 mmol), tris (dibenzylideneacetone)dipalladium(0) (0.015 g, 0.015 mmol) and (S)-(−)-2,2'-bis(diphenylphosphino)-1,1'-binaphthyl (0.030 g, 0.047 mmol) in 8 mL of anhydrous toluene, the title compound (0.1 g), contaminated with 10% of ethyl-4-iodo-benzoate, was obtained. Some 5-(isopropyl)amino-3,3,7-trimethyl-2,3-dihydro-benzofuran (Compound 33, 0.21 g) was recovered. $^1$H NMR (300 MHz, CDCl$_3$): δ 7.82 (d, 2H, J=9.1 Hz), 6.68 (d, 1H, J=2.3 Hz), 6.66 (d, 1H, J=2.3 Hz), 6.51 (d, 2H, J=9.1 Hz), 4.35–4.27 (m, 3H), 4.31 (s, 2H), 2.22 (s, 3H), 1.35–1.30 (m, 3H), 1.34 (s, 6H), 1.15 (d, 6H, J=6.5 Hz).

4-[Isopropyl-(3,3-dimethyl-7-ethyl-2,3-dihydro-benzofuran-5-yl)-amino]-benzoic acid ethyl ester (Compound 38)

Following general procedure E and using 3,3-dimethyl-7-ethyl-5-(isopropyl)amino-2,3-dihydro-benzofuran (Compound 34, 0.43 g, 1.96 mmol), ethyl-4-iodo-benzoate (0.45 g, 1.93 mmol), cesium carbonate (0.88 g, 2.7 mmol), tris(dibenzylideneacetone)dipalladium(0) (0.020 g, 0.020 mmol) and (S)-(−)-2,2'-bis(diphenylphosphino)-1,1'-binaphthyl (0.040 g, 0.064 mmol) in 6 mL of anhydrous toluene, the title compound (0.23 g, 32%) was obtained. This reaction was conducted in a sealed tube for 7 days. Some 3,3-dimethyl-7-ethyl-5-(isopropyl)amino-2,3-dihydro-benzofuran (Compound 34) was recovered. $^1$H NMR (300 MHz, CDCl$_3$): δ 7.82 (d, 2H, J=9.0 Hz), 6.69 (d, 1H, J=2.0 Hz), 6.66 (d, 1H, J=2.0 Hz), 6.51 (d, 2H, J=9.0 Hz), 4.38–4.26 (m, 5H), 2.60 (q, 2H, J=7.5 Hz), 1.33 (t, 3H, J=7.1 Hz), 1.32 (s, 6H), 1.21 (t, 3H, J=7.5 Hz), 1.15 (d, 6H, J=6.5 Hz)

4-[Isopropyl-(3,3-dimethyl-7-isopropyl-2,3-dihydro-benzofuran-5-yl)-amino]-benzoic acid ethyl ester (Compound 39)

Following general procedure E and using 3,3-dimethyl-7-isopropyl-5-(isopropyl)amino-2,3-dihydro-benzofuran (Compound 35, 0.21 g, 0.86 mmol), ethyl-4-iodo-benzoate (0.0.29 g, 1.03 mmol), cesium carbonate (0.39 g, 1.2 mmol), tris(dibenzylideneacetone)dipalladium(0) (0.020 g, 0.020 mmol) and (S)-(−)-2,2'-bis(diphenylphosphino)-1,1'-binaphthyl (0.04 g, 0.064 mmol) in 6 mL of anhydrous toluene, the title compound (0.027 g) was obtained; some of the product was eluted as a mixture with the starting amine. Some 5-(isopropyl)amino-3,3-dimethyl-7-isopropyl-2,3-dihydro-benzofuran (Compound 35) was also recovered. $^1$H NMR (300 MHz, CDCl$_3$): δ 7.82 (d, 2H, J=9.2 Hz), 6.72 (d, 1H, J=2.0 Hz), 6.64 (d, 1H, J=2.0 Hz), 6.50 (d, 2H, J=9.0 Hz), 4.40–4.26 (m, 5H), 3.10 (heptet, 1H, J=7.0 Hz), 1.34 (t, 3H, J=7.1 Hz), 1.33 (s, 6H), 1.23 (d, 6H, J=7.0 Hz), 1.15 (d, 6H, J=6.5 Hz).

4-[Isopropyl-(7-t-butyl-3,3-dimethyl-2,3-dihydro-benzofuran-5-yl)-amino]-benzoic acid ethyl ester (Compound 40)

Following general procedure E and using 7-t-butyl-3,3-dimethyl-5-(isopropyl)amino-2,3-dihydro-benzofuran (Compound 36, 0.63 g, 2.4 mmol), ethyl-4-iodo-benzoate (0.6$^2$3 g, 2.9 mmol), cesium carbonate (1.12 g, 3.4 mmol), tris(dibenzylideneacetone)dipalladium(0) (0.025 g, 0.025 mmol) and (S)-(−)-2,2'-bis(diphenylphosphino)-1,1'-binaphthyl (0.050 g, 0.079 mmol) in 10 mL of anhydrous toluene, the title compound (0.15 g) contaminated with 67% of 7-t-butyl-3,3-dimethyl-5-(isopropyl)amino-2,3-dihydro-benzofuran (Compound 36) was obtained.

4-[Isopropyl-(3,3,7-trimethyl-2,3-dihydro-benzofuran-5-yl)-amino]-benzoic acid (Compound 41)

Following general procedure H using 4-[isopropyl-(3,3,7-trimethyl-2,3-dihydro-benzofuran-5-yl)-amino]-benzoic acid ethyl ester (Compound 37, 0.08, 0.21 mmol) and 2.5 mL of 4M potassium hydroxide solution in 4 mL of ethanol, the title compound (0.055 g, 77%) was obtained as an off-white solid. $^1$H NMR (300 MHz, CDCl$_3$): δ 7.87 (d, 2H, J=8.9 Hz), 6.69 (d, 1H, J=2.0 Hz), 6.66 (d, 1H, J=2.0 Hz), 6.52 (d, 2H, J=9.1 Hz), 4.36(heptet, 1H, J=6.5 Hz), 4.32 (s, 2H), 2.23(s, 3H), 1.35 (s, 6H), 1.17 (d, 6H, J=6.5 Hz).

4-[Isopropyl-(3,3-dimethyl-7-ethyl-2,3-dihydro-benzofuran-5-yl)-amino]-benzoic acid (Compound 42)

Following general procedure I and using 4-[isopropyl-(3,3-dimethyl-7-ethyl-2,3-dihydro-benzofuran-5-yl)-amino]-benzoic acid ethyl ester (Compound 38, 0.21 g, 0.55 mmol) and 2 mL of 5M potassium hydroxide solution in 10 mL of ethanol, the title compound (0.16 g, 88%)was obtained as a white solid. $^1$H NMR (300 MHz, CDCl$_3$): δ 7.86 (d, 2H, J=9.1 Hz), 6.69 (d, 1H, J=2.0 Hz), 6.65 (d, 1H, J=2.0 Hz), 6.51 (d, 2H, J=9.1 Hz), 4.35 (heptet, 1H, J=6.5 Hz), 4.30 (s, 2H), 2.60 (q, 2H, J=7.5 Hz), 1.33 (s, 6H), 1.21 (t, 3H, J=7.5 Hz), 1.15 (d, 6H, J=6.5 Hz).

[Isopropyl-(3,3-dimethyl-7-isopropyl-2,3-dihydro-benzofuran-5-yl)-amino]-benzoic acid (Compound 43). Following general procedure I and using 4-[isopropyl-(3,3-dimethyl-7-isopropyl-2,3-dihydro-benzofuran-5-yl)-amino]-benzoic acid ethyl ester [(Compound 39, 0.15 g, contaminated with 3,3-dimethyl-7-isopropyl-5-(isopropyl)amino-2,3-dihydro-benzofuran (Compound 35)] and 2 mL of 5M sodium hydroxide in 10 mL of ethanol, the title compound (0.043 g, 13.4% for 2 steps) was obtained as a white solid. $^1$H NMR (300 MHz, CDCl$_3$): δ 7.86 (d, 2H, J=9.0 Hz), 6.71 (d, 1H, J=2.0 Hz), 6.64 (d, 1H, J=2.0 Hz), 6.51 (d, 2H, J=9.0 Hz), 4.36 (heptet, 1H, J=6.4 Hz), 4.30 (s, 2H), 3.09 (heptet, 1H, J=6.9 Hz), 1.33 (s, 6H), 1.23 (d, 6H, J=6.9 Hz), 1.15 (d, 6H, J=6.4 Hz).

4-[Isopropyl-(7-t-butyl-3,3-dimethyl-2,3-dihydro-benzofuran-5-yl)-amino]-benzoic acid (Compound 44)

Following general procedure H and using 4-[isopropyl-(7-t-butyl-3,3-dimethyl-2,3-dihydro-benzofuran-5-yl)-amino]-benzoic acid ethyl ester (Compound 40, 0.1 5 g contaminated with 67% of 5-(isopropyl)amino-7-t-butyl-3,3-dimethyl-2,3-dihydro-benzofuran (Compound 36) and 2.5 mL of 4M potassium hydroxide solution in 4 mL of ethanol, the title compound (0.034 g, 3.7% for 2 steps) was obtained. $^1$H NMR (300 MHz, CDCl$_3$): δ 7.86(d, 2H, J=9.0 Hz), 6.75 (d, 1H, J=2.1 Hz), 6.66 (d, 1H, J=2.1 Hz), 6.51 (d, 2H, J=9.1 Hz), 4.36 (heptet, 1H, J=6.5 Hz), 4.28 (s, 2H), 1.34 (s, 9H), 1.32(s, 6H), 1.15 (d, 6H, J=6.5 Hz).

4-Bromo-2-(2-chloro-1,1-dimethyl-ethyl)-5-methyl-phenol (Compound 46)

Concentrated sulfuric acid (1.75 g, 17.8 mmol) was added drop wise to a cooled (ice bath) mixture of 4-bromo-5-methyl-phenol (Compound 45, 10 g, 53.46 mmol) and 3-chloro-2-methyl-propene (5.28 mL, 53.46 mmol). The dark reaction mixture was allowed to warm to ambient temperature and stirred a total of 2 hours. The reaction mixture was diluted with water, and extracted with diethyl-ether. The combined organic extract was washed with brine, dried over anhydrous sodium sulfate, filtered and evaporated to an oil. Flash column chromatography using 3% ethyl acetate in hexanes as the eluent afforded the title compound (6.2 g, 48%) as a green solid; 4-bromo-5-methyl-phenol was recovered. $^1$H NMR (300 MHz, CDCl$_3$): δ 7.35 (s, 1H), 6.54 (s, 1H), 5.02 (s, 1H), 3.96 (s, 2H), 2.28 (s, 3H), 1.44 (s, 6H).

5-Bromo-3,3,6-trimethyl-2,3-dihydro-benzofuran (Compound 47)

To a stirred, cooled (ice bath) suspension of sodium hydride (60% dispersion in mineral oil, 1.23 g, 30.85 mmol) in 50 mL of anhydrous tetrahydrofuran under argon, a solution of 4-bromo-2-(2-chloro-1,1-dimethyl-ethyl)-5-methyl-phenol (Compound 46, 6.2 g, 25.7 mmol) in 10 mL of anhydrous tetrahydrofuran was added. After 0.5 hour, the excess sodium hydride was quenched with methanol and the reaction mixture was evaporated in vacuo. The residue was diluted with water, extracted with ether and the organic phase was washed with brine. The organic extract was dried over anhydrous sodium sulfate, filtered and evaporated to an oil. Flash column chromatography of the oil over silica gel using hexanes as the eluent afforded the title compound as a clear oil (5.25 g, quantitative). $^1$H NMR (300 MHz, CDCl$_3$): δ 7.23 (s, 1H), 6.70 (s, 1H), 4.24 (s, 2H), 2.35 (s, 3H), 1.33 (s, 6H).

1-(5-Bromo-3,3,6-trimethyl-2,3-dihydro-benzofuran-7-yl)-ethanone (Compound 48)

A stirred, cooled (ice-bath) suspension of aluminum chloride (6.85 g, 51.4 mmol) in 50 mL of anhydrous dichloromethane was treated with acetyl chloride (3.7 mL, 51.4 mmol) under argon. A solution of 5-bromo-3,3,3-trimethyl-2,3-dihydro-benzofuran (Compound 47, 5.$^2$5 g, 25.7 mmol) in 10 mL of anhydrous dichloromethane was cannulated into the clear solution, and the resulting deep red solution was allowed to warm to ambient temperature over 1 hour. The reaction mixture was poured onto iced water and extracted with dichloromethane. The combined organic extract was dried over anhydrous sodium sulfate, filtered and evaporated to a dirty white solid. Flash column chromatography on silica gel using 6% ethyl acetate in hexane as the eluent afforded the title compound (4.5 g, 61.6%). $^1$H NMR (300 MHz, CDCl$_3$): δ 7.30 (s, 1H), 4.28 (s, 2H), 2.56 (s, 3H), 2.34 (s, 3H), 1.33 (s, 6H).

2-(5-Bromo-3,3,6-trimethyl-2,3-dihydro-benzofuran-7-yl)-propan-2-ol (Compound 49)

A stirred, cooled (ice bath) solution of 1-(5-bromo-3,3,6-trimethyl-2,3-dihydro-benzofuran-7-yl)-ethanone (Compound 48, 2.0 g, 7.09 mmol), was treated drop wise with a 3M solution of methylmagnesium bromide in diethylether (2.84 mL, 8.51 mmol) and the resulting reaction mixture was stirred at ambient temperature for 2 hours. The reaction mixture was cooled (ice bath), quenched with saturated ammonium chloride solution and extracted with ether. The organic extract was washed with brine and dried over anhydrous sodium sulfate, filtered and evaporated to a residue which on flash column chromatography using 7% ethyl acetate in hexanes as the eluent afforded the title compound (I.51 g, 71.5%) as a white solid. $^1$H NMR (300 MHz, CDCl$_3$): δ 7.21 (s, 1H), 4.35 (s, 1H), 4.22 (s, 2H), 2.53 (s, 3H), 1.67 (s, 6H), 1.31 (s, 6H).

5-Bromo-7-isopropyl-3,3,6-trimethyl-2,3-dihydro-benzofuran (Compound 50)

A stirred, cooled (ice bath)solution of 2-(5-bromo-3,3,6-trimethyl-2,3-dihydro-benzofuran-7-yl)-propan-2-ol (Compound 49, 1.51 g, 5.03 mmol) in 15 mL of dichloromethane was treated with triethyl silane (1.4 mL, 8.76 mmol) followed by trifluoroacetic acid (0.65 mL, 8.43 mmol) and the resulting clear, colorless solution was stirred at ambient temperature overnight. The reaction mixture was cooled, treated with 6 mL each of methanol and water, neutralized cautiously with saturated sodium bicarbonate solution and extracted with diethylether. The organic extract was dried over anhydrous sodium sulfate, filtered and evaporated to an oil. Flash column chromatography using 0.5% ethyl acetate in hexanes as the eluent afforded the title compound (1.36 g, 95%) as an oil. $^1$H NMR (300 MHz, CDCl$_3$): δ 7.11 (s, 1H), 4.18 (s, 2H), 3.25 (heptet, 1H, J=7.1 Hz), 2.40 (s, 3H), 1.30 (s, 6H), 1.31 (d, 6H, J=7.1 Hz).

5-Bromo-7-t-butyl-3,3,6-trimethyl-2,3-dihydro-benzofuran (Compound 51)

A 2M solution of dimethylzinc in toluene (14.2 mL, 28.4 mmol) was added to a cooled (−40° C.) solution of titanium (IV)chloride solution in dichloromethane (17.5 mL, 17.5 mmol), diluted further with 15 mL of anhydrous dichloromethane. After stirring the dark solution for 0.5 hour at −40° C., a solution of 1-(5-bromo-3,3,6-trimethyl-2,3-dihydro-benzofuran- 7-yl)-ethanone (Compound 48, 2.0 g, 7.09 mmol) in 5 mL of anhydrous dichloromethane was cannulated into the reagent. The resulting reaction mixture was allowed to warm to ambient temperature and stirred overnight. The reaction was quenched with saturated ammonium chloride solution and extracted with diethylether. The organic extract was washed with brine, dried over anhydrous sodium sulfate, filtered and evaporated to an oily residue which on flash column chromatography using 1w% ethyl acetate in hexanes as the eluent afforded the title compound (1.25 g, 60%) as a clear oil. $^1$H NMR (300 MHz, CDCl$_3$): δ 7.15 (s, 1H), 4.10 (s, 2H), 2.55 (s, 3H), 1.49 (s, 9H), 1.28 (s, 6H).

7-Isopropyl-5-[(4-methoxy-phenyl)-amino]-3,3,6-trimethyl-2,3-dihydro-benzofuran (Compound 52) General Procedure K:

A mixture of 5-bromo-7-isopropyl-3,3,6-trimethyl-2,3-dihydro-benzofuran (Compound 50, 0.56 g, 1.98 mmol), p-anisidine (0.48 g, 3.96 mmol), sodium tert-butoxide (0.27 g, 2.77 mmol), tris(dibenzylideneacetone)dipalladium(0) (0.020 g, 0.02 1 mmol) and (S)-(−)-2,2'-bis(diphenylphosphino)-1,1'-binaphthyl (0.040 g, 0.064 mmol) in 6 mL of anhydrous toluene was heated at 80° C. under argon overnight. The reaction mixture was cooled to ambient temperature, diluted with diethylether and filtered. The filtrate was evaporated in vacuo to a residue which on flash column chromatography using 10% ethyl acetate in hexane as the eluent afforded the title compound (0.6 g, 93%) as a pink solid. $^1$H NMR (300 MHz, CDCl$_3$): δ 6.76 (d, 2H, J=8.9 Hz), 6.75 (s, 1H), 6.61 (d, 2H, J=8.9 Hz), 5.0 (s, 1H), 4.15 (s, 2H), 3.71 (s, 3H), 3.24 (heptet, 1H, J=7.0 Hz), 2.17 (s, 3H), 1.33 (d, 6H, J=7.0 Hz), 1.25 (s, 6H).

7-t-Butyl-5-[(4-methoxy-phenyl)-amino]-3,3,6-trimethyl-2,3-dihydro-benzofuran (Compound 53)

Following general procedure K and using 5-bromo-7-t-butyl-3,3,6-trimethyl-2,3-dihydro-benzofuran (Compound 51, 0.33 g, 1.1 mmol), p-anisidine (0.25 g, 2 mmol), sodium tert-butoxide (0.2 g, 2.1 mmol), tris(dibenzylideneacetone) dipalladium(0) (0.030 g, 0.03 mmol) and (S)-(−)-2,2'-bis(diphenylphosphino)-1,1'-binaphthyl (0.060 g, 0.096 mmol) in 3 mL of anhydrous toluene, the title compound (0.37 g, quantitative yield) was obtained as a pink solid. $^1$H NMR (300 MHz, C$_6$D$_6$): δ 6.79 (d, 2H, J=8.9 Hz), 6.72 (s, 1H), 6.60 (d, 2H, J=8.7 Hz), 4.60 (br s, 1H), 3.90 (s, 2H), 3.35 (s, 3H), 2.37 (s, 3H), 1.68(s, 9H), 1.02 (s, 6H).

5-[Ethyl-(4-methoxy-phenyl)-amino]-7-isopropyl-3,3,6-trimethyl-2,3-dihydro-benzofuran (Compound 54) General Procedure L:

A stirred solution of 7-isopropyl-5-[(4-methoxy-phenyl)-amino]-3,3,6-trimethyl-2,3-dihydro-benzofuran (Compound 52, 0.2 g, 0.615 mmol) in 5 mL of anhydrous tetrahydrofuran under argon, was cooled to −78° C. and treated with 1.6M solution of n-butyllithium in hexanes (0.77 mL, 1.23 mmol). The resulting green reaction mixture was stirred for 0.5 hour at −78° C. and then treated drop wise with iodomethane (0.5 mL, 6.15 mmol) that was passed through a bed of potassium carbonate. The yellow reaction mixture was allowed to warm to room temperature, recooled to 0° C., quenched with saturated ammonium chloride solution and extracted with diethylether. The organic extract was dried over anhydrous sodium sulfate, filtered and evaporated to a residue which was subjected to flash column chromatography to afford the title compound (0.11 5 g, 51%) as a pale yellow oil. $^1$H NMR (300 MHz, CDCl$_3$): δ 6.80 (d, 2H, J=9.1 Hz), 6.74 (s, 1H), 6.45 (d, 2H, J=9.1 Hz), 4.24 (s, 2H), 3.77 (s, 3H), 3.60 (br m, 2H), 3.25 (heptet, 1H, J=7.0 Hz), 2.12 (s, 3H), 1.38 (d, 6H, J=7.0 Hz), 1.32 (s, 6H), 1.24 (t, 6H, J=7.0 Hz).

7-Isopropyl-5-[isopropyl-(4-methoxy-phenyl)-amino]-3,3,6-trimethyl-2,3-dihydro-benzofuran (Compound 55)

Following general procedure L and using 7-isopropyl-5-[(4-methoxy-phenyl)-amino]-3,3,6-trimethyl-2,3-dihydro-benzofuran (Compound 52, 0.6 g, 2.7 mmol), 1.6M solution of n-butyllithium in hexanes (2.2 mL, 3.5 mmol) and 2-iodopropane (0.9 g, 5.4 mmol) in 10mL of anhydrous tetrahydrofuran, the title compound (0.077 g, 7%) was obtained as a brown oil after separation from recovered 7-isopropyl-5-[(4-methoxy-phenyl)-amino]-3,3,6-trimethyl-2,3-dihydro-benzofuran (Compound 52, 0.2 g) by preparative normal phase HPLC using 4% ethyl acetate in hexanes as the mobile phase. $^1$H NMR (300 MHz, CDCl$_3$): δ 6.75 (d, 2H, J=9.2 Hz), 6.62 (s, 1H), 6.38 (d, 2H, J=9.2 Hz), 4.25–4.11 (m, 3H), 3.73 (s, 3H), 3.19 (heptet, 1H, J=7.0 Hz), 2.06 (s, 3H), 1.33 (d, 6H, J=7.0 Hz), 1.27 (s, 6H), 1.11 (br m, 6H).

7-t-Butyl-5-[ethyl-(4-methoxy-phenyl)-amino]-3,3,6-trimethyl-2,3-dihydro-benzofuran (Compound 56)

Following general procedure L and using 7-t-butyl-5-[(4-methoxy-phenyl)-amino]-3,3,6-trimethyl-2,3-dihydro-benzofuran (Compound 53), (0.12 g, 0.35 mmol), 1.6M solution of n-butyllithium in hexanes (0.442 mL, 0.7 mmol) and iodomethane (0.281 mL, 3.5 mmol) in 2 mL of anhydrous tetrahydrofuran, the title compound (0.11 9 g, 92%) was obtained as a brown oil. $^1$H NMR (300 MHz, CDCl$_3$): δ 6.76 (d, 2H, J=9.0 Hz), 6.72 (s, 1H), 6.41 (d, 2H, J=9.0 Hz), 4.14 (s, 2H), 3.73 (s, 3H), 2.60 (s, 3H), 1.52 (s, 9H), 1.26 (s, 6H), 1.20 (t, 3H, J=7.1 Hz).

7-t-Butyl-5-[isopropyl-(4-methoxy-phenyl)-amino]-3,3,6-trimethyl-2,3-dihydro-benzofuran (Compound 57)

Following general procedure L and using 7-t-butyl-5-[(4-methoxy-phenyl)-amino]-3,3,6-trimethyl-2,3-dihydro-benzofuran (Compound 53, 0.13 g, 0.38 mmol), 1.6M solution of n-butyllithium in hexanes (0.5 mL, 0.8 mmol) and 2-iodopropane (0.5 mL, 5 mmol) in 2 mL of anhydrous tetrahydrofuran, the title compound (0.013 g, 8.9%) was obtained as a brown oil after separation from recovered 7-t-butyl-5-[(4-methoxy-phenyl)-amino]- 3,3,6-trimethyl-2,3-dihydro-benzofuran (Compound 53, 0.07 g) by preparative normal phase HPLC using 4% ethyl acetate in hexanes as the mobile phase. $^1$H NMR (300 MHz, C$_6$D$_6$): δ 6.82 (d, 2H, J=9.1 Hz), 6.75 (s, 1H), 6.56 (d, 2H, J=9.1 Hz), 4.09(heptet, 1H, J=6.5 Hz), 3.89 (s, 2H), 3.40(s, 3H), 2.40 (s, 3H), 1.68 (s, 9H), 1.10–1.25(m, 3H), 0.99–1.10(m, 3H), 0.99 (s, 6H).

5-[Ethyl-(4-hydroxy-phenyl)-amino]-7-isopropyl-3,3,6-trimethyl-2,3-dihydro-benzofuran (Compound 58) General Procedure M:

A stirred solution of 5-[ethyl(4-methoxy-phenyl)-amino]-7-isopropyl-3,3,6-trimethyl-2,3-dihydro-benzofuran (Compound 54, 0.11 g, 0.31 mmol) in 2 mL of anhydrous dichloromethane under argon, was treated with 1.0M solution of 9-iodo-9-borabicyclo[3.3.1]nonane (B-iodo-9-BBN) in hexanes (0.38 mL, 0.38 mmol). The resulting reaction mixture was stirred for 2 hours at ambient temperature, quenched and neutralized with saturated sodium bicarbonate solution, diluted with water and extracted with dichloromethane. The organic extract was dried over anhydrous sodium sulfate, filtered and evaporated to give a pale yellow oily residue containing the title compound (0.038 g, 37%). The residue was used without further purification for the next step.

7-Isopropyl-5-[isopropyl-(4-hydroxy-phenyl)-amino]-3,3,6-trimethyl-2,3-dihydro-benzofuran (Compound 59)

Following general procedure M and using 7-isopropyl-5-[isopropyl-(4-methoxy-phenyl)-amino]-3,3,6-trimethyl-2,3-dihydro-benzofuran (Compound 55, 0.077 g, 0.21 mmol) and 1M solution of 9-iodo-9-borabicyclo[3.3.1]nonane (B-iodo-9-BBN) in hexanes (0.25 mL, 0.25 mmol) in 2 mL of anhydrous dichloromethane, the title compound (0.06 g, 77%) was obtained as a brown oil that was used in the next step without further purification.

7-t-Butyl-5-[ethyl-(4-hydroxy-phenyl)-amino]-3,3,6-trimethyl-2,3-dihydro-benzofuran (Compound 60)

Following general procedure M and using 7-t-butyl-5-[ethyl-(4-methoxy-phenyl)-amino]-3,3,6-trimethyl-2,3-dihydro-benzofuran (Compound 56, 0.12 g, 0.3 mmol) and 1M solution of 9-iodo-9-borabicyclo[3.3.1]nonane (B-iodo-9-BBN) in hexanes (0.44 mL, 0.44 mmol) in 2 mL of anhydrous dichloromethane, the title compound was obtained as a brown oil that was used in the next step without further purification.

7-t-Butyl-5-[isopropyl-(4-hydroxy-phenyl)-amino]-3,3,6-trimethyl-2,3-dihydro-benzofuran (Compound 61)

Following general procedure M and using 7-t-butyl-5-[isopropyl-(4-methoxy-phenyl)-amino]-3,3,6-trimethyl-2,3-dihydro-benzofuran (Compound 57, 0.032 g, 0.083 mmol) and 1M solution of 9-iodo-9-borabicyclo[3.3.1]nonane (B-iodo-9-BBN) in hexanes (0.2 mL, 0.2 mmol) in 0.6 mL of anhydrous dichloromethane and 1 mL of n-pentane, the title compound (0.04 g) was obtained as a brown oil that was used in the next step without further purification.

5-[Ethyl-(4-trifuoromethanesulfonyloxy-phenyl)-amino]-7-isopropyl-3,3,6-trimethyl-2,3-dihydro-benzofuran (Compound 62) General Procedure N:

A stirred solution of 5-[ethyl-(4-hydroxy-phenyl)-amino]-7-isopropyl-3,3,6-trimethyl-2,3-dihydro-benzofuran (Compound 58, 0.038 g, 0.11 mmol) in 2 mL of anhydrous dichloromethane under argon was treated with 4-dimethylaminopyridine (0.1 52 g, 0.44 mmol) followed by 2-[N,N-bis(trifluoromethylsulfonyl)amino]-5-chloropyridine (0.224 g, 0.22 mmol) and the resulting reaction mixture was stirred at ambient temperature for 1 hour. The reaction mixture was diluted with dichloromethane and washed with water, 3% hydrochloric acid and brine. The organic phase was dried over anhydrous sodium sulfate, filtered and evaporated to a residue which on flash column chromatography using 5% ethyl acetate in hexanes afforded the title compound (0.038 g, 84%) as a colorless oil. $^1$H NMR (300 MHz, CDCl$_3$): δ 7.00 (d, 2H, J=9.2 Hz), 6.67 (s, 1H), 6.39 (d, 2H, J=9.2 Hz), 4.22 (s, 2H), 3.72 (m, 1H), 3.42 (m, 1H), 3.21 (heptet, 1H, J=6.9 Hz), 2.03 (s, 3H), 1.34 (d, 6H, J=6.9 Hz), 1.30 (s, 6H), 1.22 (t, 6H, J=7.0 Hz).

7-Isopropyl-5-[isopropyl-(4-trifluoromethanesulfonyloxy-phenyl)-amino]-3,3,6-trimethyl-2,3-dihydro-benzofuran (Compound 63)

Following general procedure N and using 7-isopropyl-5-[isopropyl-(4-hydroxy-phenyl)-amino]-3,3,6-trimethyl-2,3-dihydro-benzofuran (Compound 59, 0.074 g, 0.21 mmol), 4-dimethylaminopyridine (0.102 g, 0.84 mmol) and 2-[N,N-bis(trifluoromethylsulfonyl)amino]-5-chloropyridine (0.165 g, 0.42 mmol) in 2 mL of anhydrous dichloromethane, the title compound (0.052 g, 51%) was obtained as a colorless oil. $^1$H NMR (300 MHz, CDCl$_3$): δ 7.00 (d, 2H, J=9.3 Hz), 6.58 (s, 1H), 6.37 (d, 2H, J=9.3 Hz), 4.25–4.15 (m, 3H), 3.18 (heptet, 1H, J=7.0 Hz), 2.01 (s, 3H), 1.35–1.25 (m, 12H), 0.97 (d, 6H, J=6.6 Hz).

7-t-Butyl-5-[ethyl-(4-trifuoromethanesulfonyloxy-phenyl)-amino]-3,3,6-trimethyl-2,3-dihydro-benzofuran (Compound 64)

Following general procedure N and using 7-t-butyl-5-[ethyl-(4-hydroxy-phenyl)-amino]-3,3,6-trimethyl-2,3-dihydro-benzofuran (Compound 60, 0.12 g, 0.34 mmol), 4-dimethylaminopyridine (0.1 66 g, 1.36 mmol) and 2-[N,N-bis(trifluoromethylsulfonyl)amino]-5-chloropyridine (0.267 g, 0.68 mmol) in 2 mL of anhydrous dichloromethane, the title compound (0.110 g, 67%) was obtained after flash column chromatography using 2% ethyl acetate in hexanes as the eluent. $^1$H NMR (300 MHz, CDCl$_3$): δ 7.00 (d, 2H, J=9.3 Hz), 6.69 (s, 1H), 6.38 (d, 2H, J=9.3 Hz), 4.16 (s, 2H), 3.78–3.66 (m, 1H), 3.43–3.31 (m, 1H), 2.20 (s, 3H), 1.52 (s, 9H), 1.28 (s, 3H), 1.27 (s, 3H), 1.22 (t, 3H, J=7.1 Hz).

7-t-Butyl-5-[isopropyl-(4-trifluoromethanesulfonyloxy-phenyl)-amino]-3,3,6-trimethyl-2,3-dihydro-benzofuran (Compound 65)

Following general procedure N and using 7-t-butyl-5-[isopropyl-(4-hydroxy-phenyl)-amino]-3,3,6-trimethyl-2,3-dihydro-benzofuran (Compound 61, 0.032 g, 0.083 mmol), 4-dimethylaminopyridine (0.05 g, 0.41 mmol) and 2-[N,N-bis(trifluoromethylsulfonyl)amino]-5-chloropyridine (0.08 g, 0.22 mmol) in 1 mL of anhydrous dichloromethane, the title compound (0.032 g, 77%) was obtained after flash column chromatography using 5% ethyl acetate in hexanes as the eluent. $^1$H NMR (300 MHz, CDCl$_3$): δ 7.00 (d, 2H, J=9.3 Hz), 6.60 (s, 1H), 6.38 (d, 2H, J=9.3 Hz), 4.20(heptet, 1H, J=6.6 Hz), 4.17 (s, 2H), 2.20 (s, 3H), 1.52 (s, 9H), 1.29–1.26 (m, 9H), 0.98 (d, 3H, J=6.6 Hz).

4-[Ethyl-(3,3,6-trimethyl-7-isopropyl-2,3-dihydro-benzofuran-5-yl)-amino]-benzoic acid methyl ester (Compound 66) General Procedure O:

A solution of 5-[ethyl-(4-trifuoromethanesulfonyloxy-phenyl)-amino]-7-isopropyl-3,3,6-trimethyl-2,3-dihydro-benzofuran (Compound 62, 0.038 g, 0.11 mmol), triethyl amine (0.2 mL, 0.14 mmol), palladium(II)acetate (0.025 g, 0.11 mmol) and 1,3-bis(diphenylphosphino)propane (0.041 g, 0.1 mmol) in a mixture of 1.5 mL of methanol, 1 mL of dimethylsulfoxide and 0.5 mL of 1,2-dichloroethane was heated at 70° C. under an atmosphere of carbon monoxide overnight. The reaction mixture was cooled to ambient temperature, diluted with water and extracted with diethyl-ether. The organic extract was dried over anhydrous sodium sulfate, filtered and evaporated to a residue which on flash column chromatography using 10% ethyl acetate in hexanes afforded the title compound (0.035 g, 77%) as a pale yellow oil. $^1$H NMR (300 MHz, CDCl$_3$): δ 7.83 (d, 2H, J=9.1 Hz), 6.69 (s, 1H), 6.42 (d, 2H, J=9.1 Hz), 4.24 (s, 2H), 3.89–3.75 (m, 1H), 3.84 (s, 3H), 3.53–3.40 (m, 1H), 3.22 (heptet, 1H, J=7.0 Hz), 2.03 (s, 3H), 1.37–1.20 (m, 15H).

4-[Isopropyl-(7-isopropyl-3,3,6-trimethyl-2,3-dihydro-benzofuran-5-yl)-amino]-benzoic acid methyl ester (Compound 67)

Following general procedure O and using 7-isopropyl-5-[isopropyl-(4-trifluoromethanesulfonyloxy-phenyl)-amino]-3,3,6-trimethyl-2,3-dihydro-benzofuran (Compound 63, 0.052 g, 0.107 mmol), triethyl amine (0.4 mL, 0.28 mmol), palladium(II)acetate (0.030 g, 0.13 mmol) and 1,3-bis(diphenylphosphino)propane (0.041 g, 0.1 mmol) in a mixture of 3 mL of methanol, 2 mL of dimethylsulfoxide and 1 mL of 1,2-dichloroethane, the title compound (0.037 g, 84%) was obtained as a brown oil. $^1$H NMR (300 MHz, CDCl$_3$): δ 7.81 (d, 2H, J=9.2 Hz), 6.59 (s, 1H), 6.40 (d, 2H, J=9.2 Hz), 4.32 (heptet, 1H, J=6.6 Hz), 4.24 (s, 2H), 3.83 (s, 3H), 3.19 (heptet, 1H, J=7.0 Hz), 2.00 (s, 3H), 1.36–1.26 (m, 15H), 0.98 (d, 3H, J=6.6 Hz).

4-[Ethyl-(7-t-butyl-3,3,6-trimethyl-2,3-dihydro-benzofuran-5-yl)-amino]-benzoic acid methyl ester (Compound 68)

Following general procedure O using 7-t-butyl-5-[ethyl-(4-trifluoromethanesulfonyloxy-phenyl)-amino]-3,3,6-trimethyl-2,3-dihydro-benzofuran (Compound 64, 0.110 g, 0.22 mmol), triethyl amine (0.4 mL, 0.28 mmol), palladium (II)acetate (0.030 g, 0.13 mmol) and 1,3-bis (diphenylphosphino)propane (0.041 g, 0.1 mmol) in a mixture of 3 mL of methanol, 2 mL of dimethylsulfoxide and 1 mL of 1,2-dichloroethane, the title compound (0.093 g, quantitative yield) was obtained as a brown oil. $^1$H NMR (300 MHz, CDCl$_3$): δ 7.82 (d, 2H, J=9.1 Hz), 6.69 (s, 1H), 6.41 (d, 2H, J=9.1 Hz), 4.17 (s, 2H), 3.88–3.76 (m, 4H), 3.45–3.30 (m, 1H), 2.20 (s, 3H), 1.52 (s, 9H), 1.29 (s, 3H), 1.27 (s, 3H), 1.25 (t, 3H, J=7.1 Hz).

4-[Isopropyl-(7-t-butyl-3,3-dimethyl—2,3-dihydro-benzofuran-5-yl)-amino]-benzoic acid methyl ester (Compound 69)

Following general procedure O and using 7-t-butyl-5-[isopropyl-(4-trifluoromethanesulfonyloxy-phenyl)-amino]-3,3,6-trimethyl-2,3-dihydro-benzofuran (Compound 65, 0.018 g, 0.036 mmol) triethyl amine (0.2 mL, 0.14 mmol), palladium(II)acetate (0.025 g, 0.1 mmol) and 1,3-bis (diphenylphosphino)propane (0.041 g, 0.1 mmol) in a mixture of 1.5 mL of methanol, 1 mL of dimethylsulfoxide and 0.5 mL of 1,2-dichloroethane, the title compound (0.015 g, 98%) was obtained as a brown oil. $^1$H NMR (300 MHz, CDCl$_3$): δ 7.82 (d, 2H, J=9.1 Hz), 6.61 (s, 1H), 6.41 (d, 2H, J=9.1 Hz), 4.31 (heptet, 1H, J=6.5 Hz), 4.18 (s, 2H), 3.83(s, 3H), 2.20 (s, 3H), 1.52 (s, 9H), 1.30 (d, 3H, J=6.6 Hz), 1.29 (s, 3H), 1.27 (s, 3H), 0.99 (d, 3H, J=6.66 Hz).

4-[Ethyl-(7-isopropyl-3,3,6-trimethyl-2,3-dihydro-benzofuran-5-yl)-amino]-benzoic acid (Compound 70) General Procedure P:

A solution of 4-[ethyl-(7-isopropyl-3,3,6-trimethyl-2,3-dihydro-benzofuran-5-yl)-amino]-benzoic acid methyl ester (Compound 66, 0.035 g, 0.085 mmol) in 5 mL of methanol and 2 mL of tetrahydrofuran was treated with 1.5 mL (7.5 mmol) of 5M solution of sodium hydroxide and heated overnight at 60° C. The reaction mixture was cooled to ambient temperature and the volatiles were removed by distillation in vacuo. The residue was diluted with water, neutralized with 10% hydrochloric acid and extracted with ethyl acetate. The organic extract was washed with water and brine and dried over anhydrous sodium sulfate, filtered and evaporated to afford the title compound (0.03 g, 96%) as a pale pink solid. 1H NMR (300 MHz, CDCl$_3$): δ 7.88 (d, 2H, J=8.6 Hz), 6.68 (s, 1H), 6.43 (d, 2H, J=8.6 Hz), 4.24 (s, 2H), 3.90–3.75 (m, 1H), 3.53–3.40 (m, 1H), 3.21 (heptet, 1H, J=7.0 Hz), 2.03 (s, 3H), 1.36–1.23 (m, 15H).

4-[Isopropyl-(7-isopropyl-3,3,6-trimethyl-2,3-dihydro-benzofuran-5-yl)-amino]-benzoic acid (Compound 71)

Following general procedure P and using 4-[isopropyl-(7-isopropyl-3,3,6-trimethyl-2,3-dihydro-benzofuran-5-yl)-amino]-benzoic acid methyl ester (Compound 67, 0.037 g, 0.096 mmol) and 1.5 mL (7.5) of 5M sodium hydroxide in 5 mL of methanol, the title compound (0.027 g, 72%) was obtained, after flash column chromatography using 15% ethyl acetate in hexanes as the eluent, as a pale yellow solid. $^1$H NMR (300 MHz, CDCl$_3$): δ 7.87 (d, 2H, J=8.9 Hz), 6.59 (s, 1H), 6.42 (d, 2H, J=8.9 Hz), 4.34 (heptet, 1H, J=6.3 Hz), 4.24 (s, 2H), 3.19 (heptet, 1H, J=7.0 Hz), 1.36–1.26 (m, 15H), 0.99 (d, 3H, J=6.53 Hz).

4-[Ethyl-(7-t-butyl-3,3,6-trimethyl-2,3-dihydro-benzofuran-5-yl)-amino]-benzoic acid (Compound 72)

Following general procedure P and using 4-[ethyl-(7-t-butyl-3,3,6-trimethyl-2,3-dihydro-benzofuran-5-yl)-amino]-benzoic acid methyl ester (Compound 68, 0.11 g, 0.29 mmol) and 2 mL (7.5) of 5M sodium hydroxide in 5 mL of methanol, the title compound (0.025 g, 23%) was obtained as a pale yellow solid, after flash column chromatography using 25% ethyl acetate in hexanes as the eluent followed by recrystallization from hexanes. $^1$H NMR (300 MHz, CDCl$_3$): δ 7.88 (d, 2H, J=9.0 Hz), 6.70 (s, 1H), 6.43 (d, 2H, J=9.0 Hz), 4.17 (s, 2H), 3.88–3.76 (m, 1H), 3.45–3.30 (m, 1H), 2.20 (s, 3H), 1.52 (s, 9H), 1.28–1.24 (m, 9H).

4-[Isopropyl-(7-t-butyl-3,3,6-trimethyl-2,3-dihydro-benzofuran-5-yl)-amino]-benzoic acid (Compound 73)

A solution of 4-[isopropyl-(7-t-butyl-3,3,6-trimethyl-2,3-dihydro-benzofuran-5-yl)-amino]-benzoic acid methyl ester (Compound 69, 0.015 g, 0.038 mmol) in 3 mL of ethanol was treated with 1M sodium hydroxide (1.5 mL, 1.5 mmol) and the resulting clear solution was heated at 80° C. for 2 hours. The volatiles were removed by distillation in vacuo and the residue was neutralized with saturated ammonium chloride solution and extracted with diethylether. The organic extract was dried over anhydrous sodium sulfate, filtered and evaporated to afford, after flash column chromatography using 25% ethyl acetate in hexanes as the eluent, the title compound (0.007 g, 48%) as a solid. $^1$H NMR (300 MHz, CDCl$_3$): δ 7.87 (d, 2H, J=9.1 Hz), 6.61 (s, 1H), 6.43 (d, 2H, J=8.9 Hz), 4.32 (heptet, 1H, J=6.5 Hz), 4.18 (s, 2H), 3.83 (s, 1H), 2.19 (s, 3H), 1.52 (s, 9H), 1.32–1.28 (m, 9H), 0.99 (d, 3H, J=6.6 Hz).

5-Nitro-1,1,3,3-tetramethyl-1,3-dihydro-isobenzofuran (Compound 77)

An ice cold solution of 1,1,3,3-tetramethyl-1,3-dihydro-isobenzofuran (Compound 76 obtained substantially in accordance with the publication *J. Chem. Soc.*, 1936, 1114; 3 g, 17.03 mmol) in 15 mL of 1:1 v/v acetic acid/acetic anhydride was treated dropwise with a solution of nitric acid (1.61 g, 25.54 mmol) in 15 mL of 1:1 v/v acetic acid/acetic anhydride. The resulting reaction mixture was stirred at room temperature overnight. The reaction mixture was taken up in diethyl ether and washed with brine. The ethereal layer was dried over anhydrous sodium sulfate, filtered and evaporated to a residue which was subjected to flash column chromatography over silica gel using 5% ethyl acetate in hexane as the eluent to afford the title compound as a white solid (3.85 g, 95%). $^1$H NMR (300 MHz, CDCl$_3$): δ 8.18 (dd, 1H, J=2.1, 8.2 Hz), 7.96 (d, 1H J=1.9 Hz), 7.23 (d, 1H, J=8.2 Hz), 1.57 (s, 6H), 1.55 (s, 6H).

5-Amino-1,1,3,3-tetramethyl-1,3-dihydro-isobenzofuran (Compound 78)

A solution of 5-nitro-1,1,3,3-tetramethyl-1,3-dihydro-isobenzofuran (Compound 77, 3.8 g, 16 mmol) in 40 mL of ethanol and 10 mL of ethyl acetate was treated with 5% Pd-C (0.38 g) and the resulting reaction mixture was stirred under an atmosphere of hydrogen for 2 days. The reaction mixture was filtered over a bed of Celite™ and the filtrate was evaporated to afford the title compound (2.9 g, 95%) with trace amount of starting material. $^1$H NMR (300 MHz, CDCl$_3$): δ 6.86 (d, 1H, J=8.1 Hz), 6.59 (dd, 1H J=2.0, 8.1 Hz), 7.03 (d, 1H, J=8.0 Hz), 3.73 (br s, 2H), 1.48 (s, 6H), 1.47 (s, 6H).

4-[(1,1,3,3-tetramethyl-1,3-dihydro-isobenzofuran-5-yl)-amino]-benzoic acid ethyl ester (Compound 79)

Following general procedure E and using 5-amino-1,1,3,3-tetramethyl-1,3-dihydro-isobenzofuran (Compound 78) (1 g, 4.82 mmol), ethyl-4-iodo-benzoate (1.4 g, 5.07 mmol), cesium carbonate (2.2 g, 6.76 mmol), tris(dibenzylideneacetone)dipalladium(0) (0.030 g, 0.03 mmol), (S)-(−)- 2,2'-bis(diphenylphosphino)-1,1'-binaphthyl (0.060 g, 0.09 mmol) in 15 mL of anhydrous toluene the title compound (1.38 g, 85%) was obtained as a yellow solid after flash column chromatography using 20% ethyl acetate in hexane as the eluent. $^1$H NMR (300 MHz, CDCl$_3$): δ 7.94 (d, 2H, J=8.7 Hz), 7.10 (dd, 1H J=1.8, 7.9 Hz), 7.03 (d, 1H, J=8.0 Hz), 6.99 (d, 2H, J=8.7 Hz), 6.89 (d, 1H, J=1.7 Hz), 6.36 (s, 1H), 4.34 (q, 2H, J=7.Hz), 1.52 (s, 6H), 1.51 (s, 6H), 1.37 (t, 3H, J=7.1 Hz).

4-[Ethyl-(1,1,3,3-tetramethyl-1,3-dihydro-isobenzofuran-5-yl)-amino]-benzoic acid ethyl ester (Compound 80) General procedure Q:

To a mixture of 4-[(1,1,3,3-tetramethyl-1,3-dihydro-isobenzofuran-5-yl)-amino]-benzoic acid ethyl ester (Compound 79, 0.2 g, 0.64 mmol) and sodiumcyanoborohydride (0.12 g, 1.92 mmol) in 5 mL of tetrahydrofuran and 5 mL of glacial acetic acid, acetaldehyde (0.28 g, 6.42 mmol) was added and the reaction mixture was stirred at room temperature for 2 hours. The reaction mixture was taken up in diethyl ether and washed with brine. The organic phase was dried over anhydrous sodium sulfate, filtered and evaporated to a residue which was subjected to flash column chromatography on silica gel to afford the title compound (0.224 g, 95%) as a white solid. $^1$H NMR (300 MHz, CDCl$_3$): δ 7.86 (d, 2H, J=8.7 Hz), 7.10 (m, 2H), 6.91 (s, 1H), 6.70 (d, 2H, J=8.8 Hz), 4.32 (q, 2H, J=7.1 Hz), 3.66 (t, 2H, J=7.1 Hz), 1.55 (s, 6H), 1.51 (s, 6H), 1.35 (t, 3H, J=7.1 Hz), 1.26 (t, 3H, J=6.9 Hz).

4-[n-Propyl-(1,1,3,3-tetramethyl-1,3-dihydro-isobenzofuran-5-yl)-amino]-benzoic acid ethyl ester (Compound 81)

Following general procedure Q and using 4-[(1,1,3,3-tetramethyl-1,3-dihydro-isobenzofuran-5-yl)-amino]-benzoic acid ethyl ester (Compound 79, 0.2 g, 0.64 mmol), sodiumcyanoborohydride (0,121 g, 1.92 mmol) and propionaldehyde (1 mL, 13.7 mmol) in 5 mL of acetic acid and 5 mL of tetrahydrofuran, the title compound (0.22 g, 90%) was obtained as a white solid. $^1$H NMR (300 MHz, CDCl$_3$): δ 7.85 (d, 2H, J=9.0 Hz), 7.08 (s, 2H), 6.90 (s, 1H), 6.67 (d, 2H, J=8.9 Hz), 4.31 (q, 2H, J=7.1 Hz), 3.66 (t, 2H, J=7.8 Hz), 1.77–1.64 (m, 2H) 1.54 (s, 6H), 1.50 (s, 6H), 1.34 (t, 3H, J=7.1 Hz), 0.94 (t, 3H, J=7.4 Hz).

4-[n-Butyl-(1,1,3,3-tetramethyl-1,3-dihydro-isobenzofuran-5-yl)-amino]-benzoic acid ethyl ester (Compound 82)

Following general procedure Q and using 4-[(1,1,3,3-tetramethyl-1,3-dihydro-isobenzofuran-5-yl)-amino]-benzoic acid ethyl ester (Compound 79, 0.2 g, 0.64 mmol), sodiumcyanoborohydride (0.121 g, 1.92 mmol) and butyraldehyde (1 mL, 11.09 mmol) in 5 mL of acetic acid and 5 mL of tetrahydrofuran, the title compound (0.21 g, 88%) was obtained as a white solid. $^1$H NMR (300 MHz, CDCl$_3$): δ 7.86 (d, 2H, J=9.1 Hz), 7.11 (d, 1H, J=8.7 Hz), 7.07 (d, 1H, J=8.1 Hz), 6.90 (s, 1H), 6.68 (d, 2H, J=8.9 Hz), 4.32 (q, 2H, J=7.1 Hz), 3.70 (t, 2H, J=7.8 Hz), 1.74–1.62 (m, 2H) 1.55 (s, 6H), 1.51 (s, 6H), 1.45–1.33 (m, 2H), 1.35 (t, 3H, J=7.1 Hz), 0.95 (t, 3H, J=7.4 Hz).

4-[Ethyl-(1,1,3,3-tetramethyl-1,3-dihydro-isobenzofuran-5-yl)-amino]-benzoic acid (Compound 83)

A solution of 4-[ethyl-(1,1,3,3-tetramethyl-1,3-dihydro-isobenzofuran-5-yl)-amino]-benzoic acid ethyl ester (Compound 80, 0.224 g, 0.6 mmol) in 20 mL of ethanol was treated with 2 mL of 5M sodium hydroxide solution and the resulting solution was heated at 55° C. for 2 hours. The volatiles were removed by distillation in vacuo and the residue was acidified using hydrochloric acid and extracted with ethyl acetate. The organic extract was washed with brine, dried over anhydrous sodium sulfate and evaporated to a residue which was recrystallized from hot ethyl acetate to afford the title compound (0.2 g, 88%) as a white solid. $^1$H NMR (300 MHz, DMSO-d$_6$): δ 12.20 (s, 1H), 7.71 (d, 2H, J=8.8 Hz), 7.25 (d, 1H, J=8.4 Hz), 7.09 (m, 2H), 6.67 (d, 2H, J=8.9 Hz), 3.76 (t, 2H, J=6.9 Hz), 1.44 (s, 6H), 1.41 (s, 6H), 1.14 (t, 3H, J=6.9 Hz).

4-[n-Propyl-(1,1,3,3-tetramethyl-1,3-dihydro-isobenzofuran-5-yl)-amino]-benzoic acid (Compound 84)

A solution of 4-[n-propyl-(1,1,3,3-tetramethyl-1,3-dihydro-isobenzofuran-5-yl)-amino]-benzoic acid ethyl ester (Compound 81, 0.22 g, 0.58 mmol) in 20 mL of ethanol was treated with 2 mL of 5M sodium hydroxide solution and the resulting solution was heated at 55° C. for 2 hours. The volatiles were removed by distillation in vacuo and the residue was acidified using hydrochloric acid and extracted with ethyl acetate. The organic extract was washed with brine, dried over anhydrous sodium sulfate and evaporated to a residue which was recrystallized from hot ethyl acetate to afford the title compound (0.12 g, 55%) as a white solid. $^1$H NMR (300 MHz, acetone-d$_6$): δ 7.80 (d, 2H, J=9.0 Hz), 7.28 (d, 1H, J=8.0 Hz), 7.04 (dd, 1H, J=8.0,1.8 Hz), 7.10 (d, 1H, J=1.8 Hz), 6.72 (d, 2H, J=8.9 Hz), 3.73 (t, 2H, J=7.8 Hz), 1.76–1.64 (m, 2H), 1.48 (s, 6H), 1.46 (s, 6H), 0.94 (t, 3H, J=7.4 Hz).

4-[n-Butyl-(1,1,3,3-tetramethyl-1,3-dihydro-isobenzofuran-5-yl)-amino]-benzoic acid (Compound 85)

A solution of 4-[n-butyl-(1,1,3,3-tetramethyl-1,3-dihydro-isobenzofuran-5-yl)-amino]-benzoic acid ethyl ester (Compound 82, 0.224 g, 0.6 mmol) in 20 mL of ethanol was treated with 2 mL of 5M sodium hydroxide solution and the resulting solution was heated at 55° C. for 2 hours. The volatiles were removed by distillation in vacuo and the residue was acidified using hydrochloric acid and extracted with ethyl acetate. The organic extract was washed with brine, dried over anhydrous sodium sulfate and evaporated to a residue which was subjected to flash column chromatography on silica gel using ethyl acetate as the eluent to afford the title compound (0.091 g, 50%) as a white solid. $^1$H NMR (300 MHz, CDCl$_3$): δ 7.90 (d, 2H, J=9.1 Hz), 7.12 (d, 1H, J=8.2 Hz), 7.09 (d, 1H, J=8.1 Hz), 6.91 (s, 1H), 6.67 (d, 2H, J=9.0 Hz), 3.71 (t, 2H, J=7.8 Hz), 1.72–1.64 (m, 2H) 1.56 (s, 6H), 1.52 (s, 6H), 1.34–1.45 (m, 2H), 0.95 (t, 3H, J=7.3 Hz).

4-[i-Propyl-(1,1,3,3-tetramethyl-1,3-dihydro-isobenzofuran-5-yl)-amino]-benzoic acid ethyl ester (Compound 86)

To a solution of 4-[(1,1,3,3-tetramethyl-1,3-dihydro-isobenzofuran-5-yl)-amino]-benzoic acid ethyl ester (Compound 79, 0.1 g, 0.32 mmol) and sodiumcyanoborohydride (0.12 g, 1.92 mmol) in 2 mL of acetone and 2 mL of acetic acid, sodiumcyanoborohydride (0.1 g, 1.58 mmol) was added followed by a drop of sulfuric acid. After half an hour at room temperature, another drop of sulfuric acid was added and the reaction mixture was stirred at room temperature for 3 days. The reaction mixture was taken up in ethyl acetate and washed with brine. The organic phase was dried over anhydrous sodium sulfate, filtered and evaporated to a residue which was subjected to flash column chromatography on silica gel, using 5% ethyl acetate in hexane as the eluent, to afford the title compound (0.007 g, <10%). $^1$H NMR (300 MHz, CDCl$_3$): δ 7.83 (d, 2H, J=9.0 Hz), 7.14 (d, 1H, J=7.9 Hz), 7.00 (dd, 1H, J=7.8, 1.8 Hz), 6.81 (d, 1H, J=1.7 Hz), 6.52 (d, 2H, J=9.2 Hz), 4.39 (heptet, 1H, J=6.6 Hz), 4.30 (q, 2H, J=7.11 Hz) 1.56 (s, 6H), 1.51 (s, 6H), 1.34 (t, 3H, J=7.1 Hz), 1.17 (d, 6H, J=6.6 Hz).

4-[i-Propyl-(1,1,3,3-tetramethyl-1,3-dihydro-isobenzofuran-5-yl)-amino]-benzoic acid (Compound 87)

A solution of 4-[i-propyl-(1,1,3,3-tetramethyl-1,3-dihydro-isobenzofuran-5-yl)-amino]-benzoic acid ethyl ester (Compound 86, 0.007 g) in 5 mL of ethanol was treated with 2 mL of 5M sodium hydroxide solution and the resulting solution was heated at 55° C. for 2 hours. The volatiles were removed by distillation in vacuo and the residue was acidified using hydrochloric acid and extracted with ethyl acetate. The organic extract was washed with brine, dried over anhydrous sodium sulfate and evaporated to a residue which was subjected to preparative reverse phase HPLC, using 10% water in acetonitrile as the mobile phase, to afford the title compound (0.0064, 90%) as a white solid. $^1$H NMR (300 MHz, acetone-d$_6$): δ 7.78 (d, 2H, J=8.9 Hz), 7.32 (d, 1H, J=7.8 Hz), 7.04 (dd, 1H, J=7.8 J=1.8 Hz), 7.00 (d, 1H, J=1.7 Hz), 6.56 (d, 2H, J=9.0 Hz), 4.46 (heptet, 1H, J=6.5 Hz), 1.50 (s, 6H), 1.47 (s, 6H), 1.15 (d, 6H, J=6.5 Hz).

What is claimed is:

1. A compound selected from compounds of Formula 1 and Formula 2,

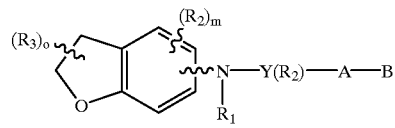

Formula 1

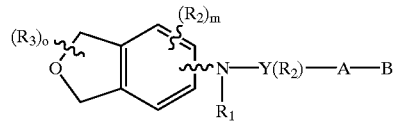

Formula 2 where R$_1$ is H, alkyl of 1 to 10 carbons, phenyl-C$_1$–C$_6$ alkyl, C$_1$–C$_6$-alkylphenyl, heteroaryl-C$_1$–C$_6$ alkyl, C$_1$–C$_6$-alkylheteroaryl where heteroaryl is selected from the group consisting of pyridyl, thienyl, furyl, pyridazinyl, pyrimidinyl, pyrazinyl, thiazolyl, oxazolyl, imidazolyl and pyrrazolyl;

R$_2$ is independently H, alkyl of 1 to 6 carbons, F, Cl, Br, I, CF$_3$, fluoro substituted alkyl of 1 to 6 carbons, OH, SH, alkoxy of 1 to 6 carbons, or alkylthio of 1 to 6 carbons;

m is an integer having the values of 0 to 3;

R$_3$ is independently H, alkyl of 1 to 6 carbons, or F;

o is an integer having the values of 0 to 4;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, tri-lower alkylsilyl, OH, OR$_8$ or OCOR$_8$ where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, or a pharmaceutically acceptable salt of said compound.

2. A compound in accordance with claim 1 where the compound has the structure of Formula 1.

3. A compound in accordance with claim 2 where the Y group is selected from phenyl, pyridyl, thienyl and furyl.

4. A compound in accordance with claim 2 where R$_1$ is alkyl of 1 to 10 carbons.

5. A compound in accordance with claim 2 where the A—B group represents (CH$_2$)$_q$COOR$_8$ or (CH$_2$)$_q$COOH where q is 0, or a pharmaceutically acceptable salt thereof.

6. A compound in accordance with claim 1 where the compound has the structure of Formula 2.

7. A compound in accordance with claim 6 where the Y group is selected from phenyl, pyridyl, thienyl and furyl.

8. A compound in accordance with claim 6 where $R_1$ is alkyl of 1 to 10 carbons.

9. A compound in accordance with claim 6 where the A—B group represents $(CH_2)_q COOR_8$ or $(CH_2)_q COOH$ where q is 0, or a pharmaceutically acceptable salt thereof.

10. A compound in accordance with claim 1 where Y is phenyl.

11. A compound in accordance with claim 2 where the amino group is attached to the 5 position of the dihydrobenzofuran moiety.

12. A compound in accordance with claim 6 where the amino group is attached to the 5 position of the 1,3-dihydroisobenzofuran moiety.

13. A compound of the formula where $R_1$ is H or alkyl of 1 to 10 carbons;

$R_2$ is independently H, alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer having the values of 0 to 3;

$R_3$ is independently H, alkyl of 1 to 6 carbons, or F, and o is in an integer having the values of 0 to 4

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, tri-lower alkylsilyl, OH, $OR_8$ or $OCOR_8$ where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$, is lower alkyl, phenyl or lower alkylphenyl, $R_{12}$ is lower alkyl, and $R_{13}$ is divalent alkyl radical of 2–5 carbons, or a pharmaceutically acceptable salt of said compound.

14. A compound in accordance with claim 13 where the phenyl group is substituted in the 1 and 4 positions by the amino and the A—B groups.

15. A compound of the formula where $R_1$ is H, alkyl of 1 to 10 carbons;

$R_2$ is independently H, alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons;

m is an integer having the values of 0 to 3;

$R_3$ is independently H, alkyl of 1 to 6 carbons, or F, and o is in an integer having the values of 0 to 4, A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, tri-lower alkylsilyl, OH, $OR_8$, or $OCOR_8$ where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

16. A compound in accordance with claim 15 where the phenyl group is substituted in the 1 and 4 positions by the amino and the A—B groups.

17. A compound of the formula where $R_1$ is H or alkyl of 1 to 6 carbons;

$R_2$ is alkyl of 1 to 6 carbons;

$R^*_2$ is H or alkyl of 1 to 6 carbons, and

B is COOH, $COOR^*_8$, OH or $OR^*_8$, where $R^*_8$ is alkyl of 1 to 6 carbons, or a pharmaceutically acceptable salt thereof.

18. A compound in accordance with claim 17 where $R_1$ is H, $R_2^*$ is H, $R_2$ is methyl, ethyl, iso-propyl or tertiary-butyl, and B is COOH or COOEt or a pharmaceutically acceptable salt thereof.

19. A compound in accordance with claim 18 where B is COOH or a pharmaceutically acceptable salt thereof.

20. A compound in accordance with claim 17 where $R_1$ is methyl, ethyl or iso-propyl, $R_2{}^*$ is H, $R_2$ is methyl, ethyl, iso-propyl or tertiary-butyl, and B is COOH or COOEt or a pharmaceutically acceptable salt thereof.

21. A compound in accordance with claim 18 where B is COOH or a pharmaceutically acceptable salt thereof.

22. A compound in accordance with claim 17 where $R_1$ is H, methyl, ethyl, iso-propyl or tertiary-butyl, $R_2{}^*$ is methyl, $R_2$ is methyl, ethyl, iso-propyl or tertiary-butyl, and B is COOH, COOMe, COOEt, OH or $OCH_3$, or a pharmaceutically acceptable salt thereof.

23. A compound in accordance with claim 22 where B is COOH or a pharmaceutically acceptable salt thereof.

24. A compound of the formula

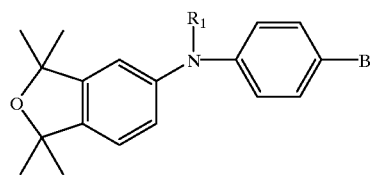

where $R_1$ is H or lower alkyl of 1 to 6 carbons, and
B is COOH, COOMe or COOEt or a pharmaceutically acceptable salt thereof.

25. A compound in accordance with claim 24 where $R_1$ is ethyl, n-propyl, i-propyl, or n-butyl.

26. A compound in accordance with claim 25 where B is COOH or a pharmaceutically acceptable salt thereof.

* * * * *

UNITED STATES PATENT AND TRADEMARK OFFICE
CERTIFICATE OF CORRECTION

PATENT NO.     : 6,093,838
DATED          : July 25, 2000
INVENTOR(S)    : Vasudevan et al.

It is certified that error appears in the above-identified patent and that said Letters Patent is hereby corrected as shown below:

Column 2,
Line 20, "$RXF_\gamma$" should be -- $RXR_\gamma$ --.

Column 3,
Line 56, "-$CH_2$,OH" should be -- -CH2OH --.

Column 6,
Line 50, "various" should be -- variations --.

Column 10,
Line 40, "mililiter" should be -- milliliter --.
Line 45, delete ":" following the word "SYNTHETIC".

Column 11,
Line 25, "often" should be -- of ten --.
Last line of Reaction Scheme 1, "tolune" should be -- toluene --.

Column 13,
Line 1,

Column 14,
Line 28, "bromoifuran" should be -- bromofuran --.

Column 15,
Line 28, "lor" should be -- for --.

Column 16,
Line 23, "1978. 34." should be -- 1978, 34, --.

Column 20,
Line 1, insert -- . -- after the word "thereof".
Line 3, "group," should be -- group --.

Column 21,
Line 2 of Reaction Scheme 4, below the first arrow, "$Pd_2$,$dba_3$" should be -- $Pd_2dba_3$ --.

UNITED STATES PATENT AND TRADEMARK OFFICE
CERTIFICATE OF CORRECTION

PATENT NO. : 6,093,838
DATED : July 25, 2000
INVENTOR(S) : Vasudevan et al.

It is certified that error appears in the above-identified patent and that said Letters Patent is hereby corrected as shown below:

Column 22,
Line 1 of Reaction Scheme 4, above the third arrow, "C." should be -- C --.
Line 3 of Reaction Scheme 4, above the second arrow, "C." should be -- C --.
Line 4 of Reaction Scheme 4, above the arrow, "C." should be -- C --.

Column 24,
First line of Reaction Scheme 4,

Line 24, "C." should be -- C --.

Column 25,
Line 3 of Reaction Scheme 6, above the first arrow, "C." should be -- C --.
Line 3 of Reaction Scheme 6, above the arrow, "NaO$^4$Bu" should be -- NaOtBu --.

Column 28,
Line 1 of Reaction Scheme 6 continued, above the row, "C." should be -- C --.
Lines 20 and 47, "C." should be -- C --.

Column 29,
Line 1, "dihydrobenzofuiran" should be -- dihydrobenzofuran --
Line 15, delete "compounds".

Column 30,
Lines 8 and 42, "C." should be -- C --.
Lines 8 and 42, delete the word "for".
Line 18, "nmr" should be -- NMR --.
Line 40, "0.01 5" should be -- 0.015 --.
Line 46, "tetrahydrofiran" should be -- tetrahydrofuran --.

Column 31,
Line 46, "C." should be -- C --.
Line 60, "115 mmol" should be -- 1.15 mmol --.

Column 32,
Line 10, "(S)-(-)- 2,2'-" should be -- (S)-(-)- 2,2'- --.
Line 22, "0.0.13" should be -- 0.13 --.
Lines 40 and 59, "C." should be -- C --.
Line 56, "0.1 6 mmol" should be -- 0.016 mmol --.
Line 58, "iodomethane" should be -- iodoethane --.

UNITED STATES PATENT AND TRADEMARK OFFICE
CERTIFICATE OF CORRECTION

PATENT NO.    : 6,093,838
DATED         : July 25, 2000
INVENTOR(S)   : Vasudevan et al.

It is certified that error appears in the above-identified patent and that said Letters Patent is hereby corrected as shown below:

Column 33,
Lines 22, 53 and 58, "iodomethane" should be -- iodoethane --.

Column 34,
Line 2, "iodomethane" should be -- iodoethane --.
Lines 16 and 43, "C." should be -- C --.

Column 36,
Line 22, insert -- ( -- before the third occurrence of "a".
Line 66, "0.0.29" should be -- 0.29 --.

Column 37,
Line 18, "0.6$^2$3" should be -- 0.623 --.
Line 29, "0.08," should be -- 0.08g, --.
Line 66, "0.1 5 g" should be -- 0.15 g --.

Column 38,
Line 48, "5.$^2$5" should be -- 5.25 --.

Column 39,
Line 7, "I51" should be -- 1.51 --.
Line 31, "C.)" should be -- C) --.
Lines 36 and 58, "C." should be -- C --.
Line 44, "1w%" should be -- 1% --.
Line 56, "0.02 1" should be -- 0.021 --.

Column 40,
Lines 21, 24 and 27, "C." should be -- C --.
Lines 25 and 62, "iodomethane" should be -- iodoethane --.
Line 32, "0.11 5 g" should be -- 0.115 g --.
Line 63, "0.11 9 g" should be -- 0.119 g --.

Column 42,
Lines 1 and 37, "trifuoromethanesulfonyloxy" should be
-- trifluoromethanesulfonyloxy --.
Line 43, "0.1 66" should be -- 0.166 --.

Column 43,
Line 4, "trifuoromethanesulfonyloxy" should be -- trifluoromethanesulfonyloxy --.
Line 11, "C." should be -- C --.
Line 61, "0.1" should be -- 0.11 --.
Line 64, "0.01 5 g" should be -- 0.015 g --.

UNITED STATES PATENT AND TRADEMARK OFFICE
CERTIFICATE OF CORRECTION

PATENT NO. : 6,093,838
DATED : July 25, 2000
INVENTOR(S) : Vasudevan et al.

It is certified that error appears in the above-identified patent and that said Letters Patent is hereby corrected as shown below:

Column 44,
Line 18, "1H" should be -- $^1H$ --.
Line 56, "C." should be -- C --.

Column 46,
Line 7, "(0,121$g_a$) should be -- (0.121g --.
Lines 38 and 56, "C." should be -- C --.

Column 47,
Lines 8 and 54, "C." should be -- C --.

Column 48,
Lines 59, 61, 63 and 65, "claim" should be -- Claim --.

Column 49,
Lines 1, 3, 6, 8, 11, 14 and 17, "claim" should be -- Claim --.
Line 60, "$R_{11}$," should be -- $R_{11}$ --.

Column 50,
Lines 42 and 64, "claim" should be -- Claim --.

Column 51,
Lines 1, 4, 9, 11 and 17, "claim" should be -- Claim --.

Column 52,
Lines 14 and 16, "claim" should be -- Claim --.

Signed and Sealed this

Twenty-sixth Day of July, 2005

JON W. DUDAS
*Director of the United States Patent and Trademark Office*